(12) United States Patent
Abunassar et al.

(10) Patent No.: US 11,504,064 B2
(45) Date of Patent: Nov. 22, 2022

(54) SYSTEMS AND METHODS FOR INTRA-PROCEDURAL CARDIAC PRESSURE MONITORING

(71) Applicant: EVALVE, INC., Santa Clara, CA (US)

(72) Inventors: Chad J. Abunassar, San Francisco, CA (US); Brandon W. Chu, San Francisco, CA (US); Patricia H. Ho, Redwood City, CA (US); Koji J. Kizuka, San Francisco, CA (US); Benjamin L. Lee, Santa Clara, CA (US); Tamer M. Mahmoud, Sunnyvale, CA (US); Sean A. McNiven, Menlo Park, CA (US); Scott C. Mosher, San Francisco, CA (US); Santosh V. Prabhu, Sunnyvale, CA (US); Lauren G. Troxler, San Francisco, CA (US); Dylan T. Van Hoven, San Carlos, CA (US)

(73) Assignee: EVALVE, INC., Santa Clara, CA (US)

( * ) Notice: Subject to any disclaimer, the term of this patent is extended or adjusted under 35 U.S.C. 154(b) by 0 days.

(21) Appl. No.: 16/321,221

(22) PCT Filed: Jul. 27, 2017

(86) PCT No.: PCT/US2017/044224
§ 371 (c)(1),
(2) Date: Jan. 28, 2019

(87) PCT Pub. No.: WO2018/022919
PCT Pub. Date: Feb. 1, 2018

(65) Prior Publication Data
US 2019/0167197 A1    Jun. 6, 2019

Related U.S. Application Data

(60) Provisional application No. 62/368,082, filed on Jul. 28, 2016.

(51) Int. Cl.
*A61B 5/00* (2006.01)
*A61B 17/00* (2006.01)
(Continued)

(52) U.S. Cl.
CPC ........ *A61B 5/6869* (2013.01); *A61B 5/02158* (2013.01); *A61B 5/6852* (2013.01);
(Continued)

(58) Field of Classification Search
CPC . A61B 5/6869; A61B 5/02158; A61B 5/6852; A61B 17/0057; A61B 17/064;
(Continued)

(56) References Cited

U.S. PATENT DOCUMENTS 3,671,979 A * 6/1972 Moulopoulos ........ A61F 2/2412
                                                        623/2.11
4,850,358 A * 7/1989 Millar ................. A61B 5/14539
                                                          600/561
(Continued)

FOREIGN PATENT DOCUMENTS

EP         1 208 867 A2    5/2002
WO    WO 2015/157709 A1   10/2015

OTHER PUBLICATIONS

International Search Report dated Jan. 2, 2018 in International Application No. PCT/US2017/044224.
(Continued)

*Primary Examiner* — Carl H Layno
*Assistant Examiner* — Manolis Pahakis
(74) *Attorney, Agent, or Firm* — Baker Botts L.L.P.

(57) ABSTRACT

The present disclosure relates to delivery devices and interventional devices configured to enable monitoring of pressure and other hemodynamic properties before, during, and/or after a cardiac procedure. A guide catheter includes a routing lumen or a routing groove for routing a sensor wire
(Continued)

to a desired location during a cardiac procedure. A guide catheter includes one or more pressure sensors positioned to provide desired pressure measurements when the guide catheter is deploying an interventional device. An interventional device may also include one or more associated sensors for providing hemodynamic information before, during, and/or after deployment.

18 Claims, 27 Drawing Sheets

(51) Int. Cl.
    *A61B 17/064* (2006.01)
    *A61B 17/12* (2006.01)
    *A61B 17/122* (2006.01)
    *A61B 5/0215* (2006.01)
(52) U.S. Cl.
    CPC ........ *A61B 17/0057* (2013.01); *A61B 17/064* (2013.01); *A61B 17/122* (2013.01); *A61B 17/12122* (2013.01); *A61B 17/12172* (2013.01); *A61B 17/12177* (2013.01); *A61B 2017/00022* (2013.01); *A61B 2017/00243* (2013.01); *A61B 2017/00575* (2013.01); *A61B 2017/00592* (2013.01); *A61B 2017/00606* (2013.01); *A61B 2017/0649* (2013.01)
(58) Field of Classification Search
    CPC ........ A61B 17/12122; A61B 17/12172; A61B 17/122; A61B 17/12177; A61B 2017/00022; A61B 2017/00243; A61B 2017/00575; A61B 2017/00592; A61B 2017/00606; A61B 2017/0649
    See application file for complete search history.

(56) References Cited

U.S. PATENT DOCUMENTS

| | | | | |
|---|---|---|---|---|
| 4,928,693 | A * | 5/1990 | Goodin | A61B 5/0215 600/434 |
| 4,966,148 | A * | 10/1990 | Millar | A61B 5/14539 600/486 |
| 6,106,477 | A * | 8/2000 | Miesel | A61B 5/6884 623/1.1 |
| 6,112,598 | A * | 9/2000 | Tenerz | A61B 5/0215 73/756 |
| 6,343,514 | B1 * | 2/2002 | Smith | A61B 5/0215 374/E1.008 |
| 6,419,674 | B1 * | 7/2002 | Bowser | A61N 1/057 606/45 |
| 6,514,249 | B1 * | 2/2003 | Maguire | A61N 7/02 606/41 |
| 6,754,608 | B2 * | 6/2004 | Svanerudh | A61B 5/028 702/130 |
| 7,329,223 | B1 * | 2/2008 | Ainsworth | A61B 5/0084 600/300 |
| 7,422,563 | B2 * | 9/2008 | Roschak | A61B 8/12 601/2 |
| 7,635,329 | B2 * | 12/2009 | Goldfarb | A61B 17/08 600/37 |
| 7,666,204 | B2 | 2/2010 | Thornton et al. | |
| 8,298,156 | B2 * | 10/2012 | Manstrom | A61B 5/14552 600/561 |
| 9,149,230 | B2 * | 10/2015 | Caron | A61B 5/6852 |
| 9,775,567 | B2 * | 10/2017 | Suchecki | A61B 5/0215 |
| 9,877,660 | B2 * | 1/2018 | O'Connell | A61B 5/02158 |
| 9,974,617 | B2 * | 5/2018 | Flexman | A61B 5/1076 |
| 10,028,667 | B2 * | 7/2018 | Kishida | G01D 5/35364 |
| 10,244,951 | B2 * | 4/2019 | Hiltner | A61B 5/02156 |
| 10,327,743 | B2 * | 6/2019 | St. Goar | A61B 17/00234 |
| 10,602,984 | B2 * | 3/2020 | Hiltner | A61M 25/09 |
| 11,090,006 | B2 * | 8/2021 | Jung, Jr. | A61B 5/0215 |
| 11,272,847 | B2 * | 3/2022 | Glover | A61B 5/0205 |
| 2001/0044633 | A1 * | 11/2001 | Klint | A61M 25/0053 606/200 |
| 2002/0165479 | A1 * | 11/2002 | Wilk | A61F 2/064 604/8 |
| 2003/0004543 | A1 * | 1/2003 | Gleeson | A61B 17/0684 606/213 |
| 2004/0082879 | A1 * | 4/2004 | Klint | A61F 2/95 600/585 |
| 2004/0092962 | A1 | 5/2004 | Thornton et al. | |
| 2005/0056292 | A1 * | 3/2005 | Cooper | A61B 18/1492 128/898 |
| 2006/0025854 | A1 * | 2/2006 | Lashinski | A61B 17/068 623/1.25 |
| 2006/0074318 | A1 * | 4/2006 | Ahmed | A61B 8/445 600/465 |
| 2006/0106298 | A1 * | 5/2006 | Ahmed | A61B 5/062 600/381 |
| 2006/0116749 | A1 * | 6/2006 | Willink | A61M 25/0084 623/1.11 |
| 2006/0149350 | A1 * | 7/2006 | Patel | A61F 2/014 623/1.11 |
| 2007/0100356 | A1 * | 5/2007 | Lucatero | A61F 2/2445 606/139 |
| 2007/0208252 | A1 * | 9/2007 | Makower | A61B 6/037 600/424 |
| 2008/0086107 | A1 * | 4/2008 | Roschak | A61M 25/0068 604/506 |
| 2008/0188921 | A1 * | 8/2008 | Yamasaki | A61B 5/062 623/1.13 |
| 2010/0234698 | A1 * | 9/2010 | Manstrom | A61B 5/02158 600/478 |
| 2010/0241008 | A1 * | 9/2010 | Belleville | A61M 25/00 600/478 |
| 2011/0301699 | A1 * | 12/2011 | Saadat | A61B 18/1477 623/2.4 |
| 2012/0184982 | A1 * | 7/2012 | Herbowy | A61B 17/12136 606/194 |
| 2013/0030303 | A1 * | 1/2013 | Ahmed | A61B 8/445 600/465 |
| 2013/0046373 | A1 * | 2/2013 | Cartledge | A61F 2/95 623/1.11 |
| 2013/0197621 | A1 * | 8/2013 | Ryan | A61B 17/0625 623/1.11 |
| 2013/0237864 | A1 * | 9/2013 | Mazar | A61B 5/02141 600/488 |
| 2013/0281979 | A1 | 10/2013 | Arnim | |
| 2013/0296692 | A1 * | 11/2013 | Vanney | A61B 5/6851 600/424 |
| 2014/0249386 | A1 * | 9/2014 | Caron | A61B 5/01 600/478 |
| 2014/0296962 | A1 * | 10/2014 | Cartledge | A61F 2/2439 623/1.12 |
| 2015/0133800 | A1 | 5/2015 | McCaffrey et al. | |
| 2015/0173673 | A1 * | 6/2015 | Toth | A61B 18/1492 600/300 |
| 2015/0196210 | A1 * | 7/2015 | McCaffrey | A61B 5/6852 600/488 |
| 2015/0272734 | A1 * | 10/2015 | Sheps | A61B 34/20 623/2.11 |
| 2015/0305633 | A1 * | 10/2015 | McCaffrey | A61B 5/0215 600/486 |
| 2015/0351645 | A1 * | 12/2015 | Hiltner | A61M 25/09 600/486 |
| 2015/0359438 | A1 * | 12/2015 | McCaffrey | A61B 5/0215 600/486 |
| 2016/0000341 | A1 * | 1/2016 | Rotman | A61B 5/0215 606/41 |
| 2016/0128583 | A1 * | 5/2016 | Caron | A61F 2/2427 600/486 |
| 2016/0128767 | A1 * | 5/2016 | Azamian | A61B 18/1492 606/41 |
| 2016/0158490 | A1 * | 6/2016 | Leeflang | A61M 25/005 604/527 |

(56) References Cited

U.S. PATENT DOCUMENTS

| | | | |
|---|---|---|---|
| 2016/0242661 A1* | 8/2016 | Fischell | A61B 5/6852 |
| 2016/0310255 A1* | 10/2016 | Purcell | A61F 2/2427 |
| 2016/0374710 A1* | 12/2016 | Sinelnikov | A61B 17/2202 |
| | | | 600/439 |
| 2017/0027458 A1* | 2/2017 | Glover | A61B 5/6851 |
| 2017/0086974 A1* | 3/2017 | Lashinski | A61F 2/2427 |
| 2017/0100250 A1 | 4/2017 | Marsot et al. | |
| 2017/0135816 A1* | 5/2017 | Lashinski | A61F 2/2439 |
| 2017/0196478 A1* | 7/2017 | Hunter | A61B 5/6847 |
| 2018/0028787 A1* | 2/2018 | McNiven | A61M 25/0026 |
| 2018/0036514 A1* | 2/2018 | Kassab | A61M 25/04 |
| 2018/0064565 A1* | 3/2018 | MacTaggart | A61B 17/12109 |
| 2018/0085559 A1* | 3/2018 | Laby | A61B 17/122 |
| 2018/0256848 A1 | 9/2018 | Ramanathan | |
| 2019/0069949 A1* | 3/2019 | Vrba | A61B 17/122 |
| 2019/0167197 A1 | 6/2019 | Abunassar et al. | |
| 2019/0239998 A1* | 8/2019 | Tuval | A61F 2/07 |
| 2020/0288950 A1* | 9/2020 | Petroff | A61B 1/00126 |
| 2021/0259835 A1* | 8/2021 | Tyler, II | A61F 2/2427 |

OTHER PUBLICATIONS

International Search Report dated Dec. 8, 2020 in International Application No. PCT/US2020/052646.

* cited by examiner

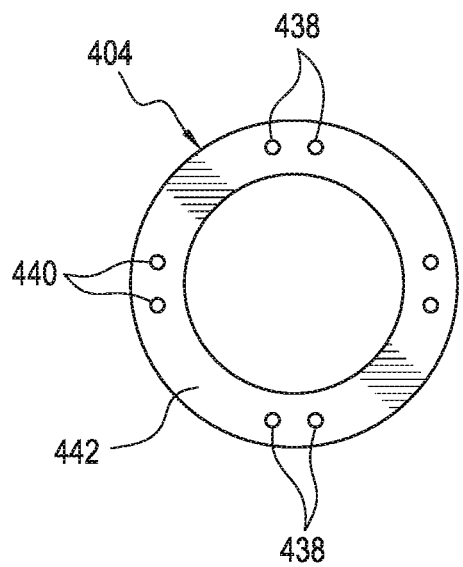
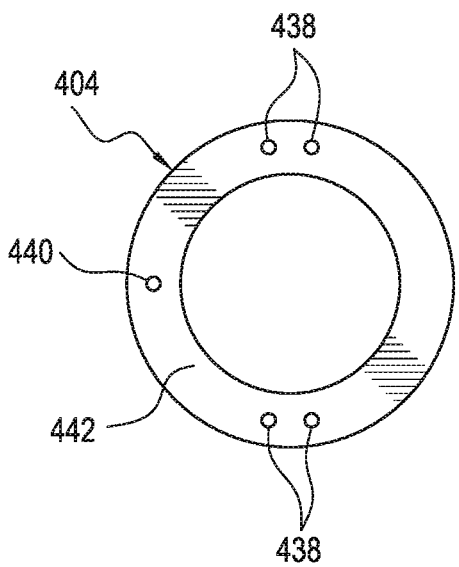
FIG. 4A  FIG. 4B
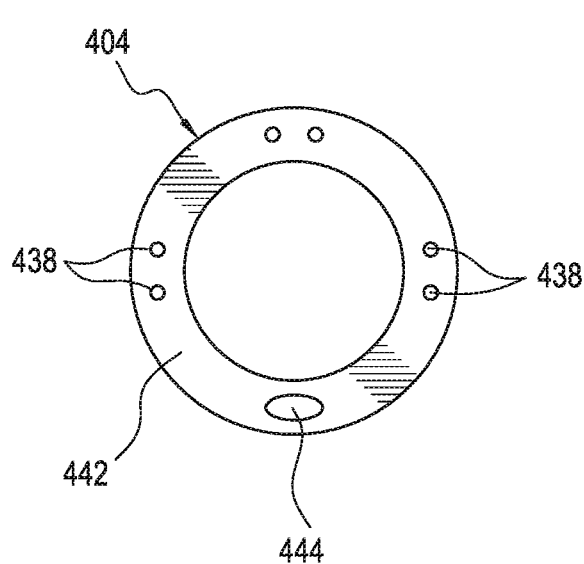
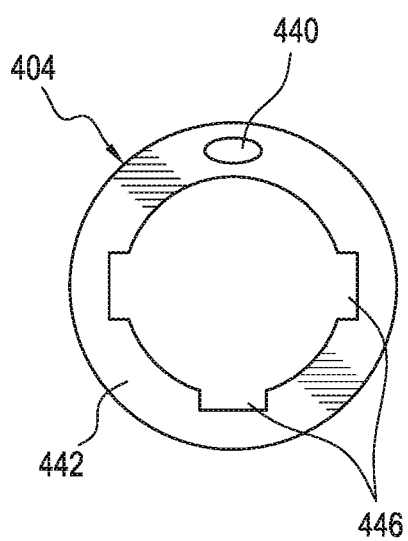
FIG. 4C  FIG. 4D

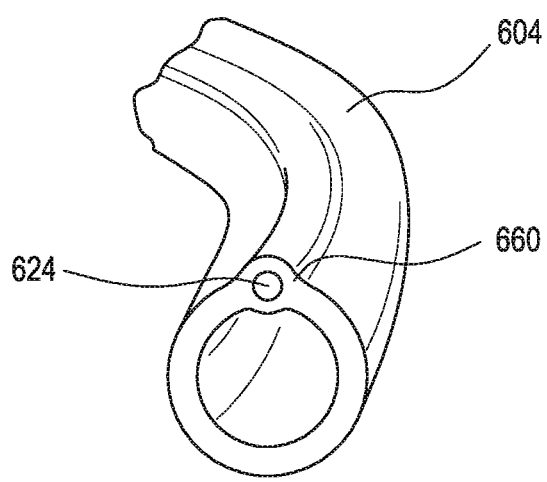
FIG. 6A
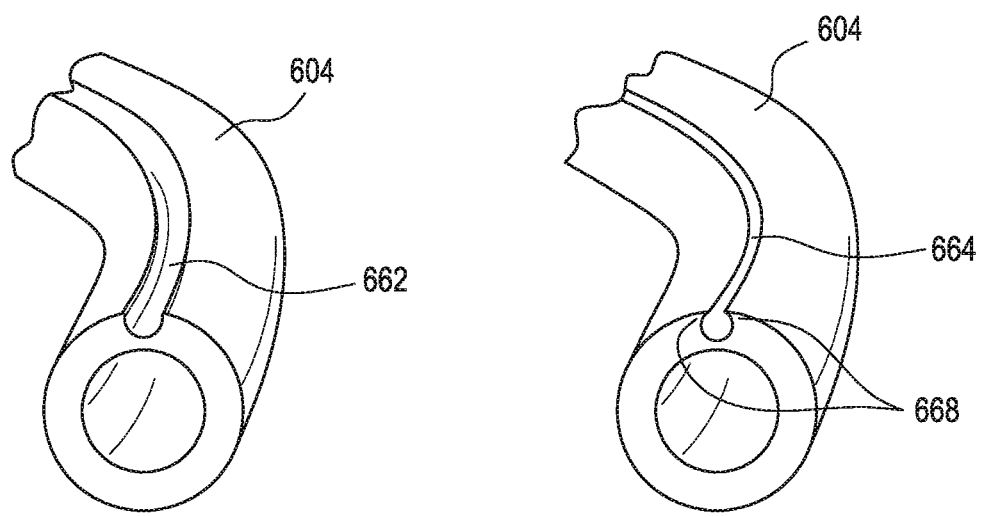
FIG. 6B
FIG. 6C

SYSTEMS AND METHODS FOR INTRA-PROCEDURAL CARDIAC PRESSURE MONITORING

CROSS-REFERENCE TO RELATED APPLICATIONS

This application is a U.S. National Stage Patent Application under 35 U.S.C. § 371 of International Application No. PCT/US2017/044224, filed on Jul. 27, 2017, which claims priority to and the benefit of U.S. Provisional Patent Application Ser. No. 62/368,082, filed Jul. 28, 2016 and titled "SYSTEMS AND METHODS FOR INTRA-PROCEDURAL CARDIAC PRESSURE MONITORING," the disclosure of each of which are incorporated herein by reference in their entirety.

BACKGROUND

During cardiac procedures, blood pressure is often measured and monitored at different areas of the heart in order to aid in initial diagnosis, to confirm procedural safety, and to verify procedural efficacy. For example, in the context of a mitral valve repair or replacement procedure, right-atrial pressure, left-atrial pressure, and pressure gradients across the mitral valve may be measured both during and after the procedure.

Typically, such pressure monitoring is achieved through the use of a pressure wire or fractional flow reserve ("FFR") wire that is inserted into the targeted treatment area of the heart. For example, an operator may introduce a pressure wire into a pulmonary vein to monitor left atrial pressure during a mitral valve repair or replacement procedure. In some circumstances, indirect imaging-based methods are also used to calculate pressure.

Although some degree of intra-procedural pressure monitoring is enabled through these methods, there are several associated limitations. For example, the use of a pressure wire or FFR wire in conjunction with guidewires, catheters, and other components of the procedure is often cumbersome and can increase procedure time with an increased risk of procedural complications. For example, in procedures that involve crossing of the septum, monitoring pressure at the targeted area may require a larger septal puncture, or a second puncture to provide access for a pressure wire to the targeted area.

In addition, such pressure monitoring often generates inaccurate and/or imprecise results. Accordingly, in many circumstances, the potential benefits of monitoring cardiac pressure intra-procedurally are negated and offset by the foregoing problems.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Certain embodiments described herein relate to interventional delivery devices configured for delivering an interventional device (such as a valve repair or replacement device, annuloplasty ring, chord replacement or repair device, spacer device, occlusion device, suturing device, or other cardiac interventional device) to a targeted treatment area. The delivery devices include one or more sensors (such as a sensor wire or sensor transducer for measuring pressure, flow, and/or other hemodynamic properties) to enable the monitoring of hemodynamic properties before, during, and/or after deployment of the interventional device.

In some embodiments, the delivery device includes an outer guide catheter having a proximal end and a distal end, an inner sleeve positioned radially within the outer guide catheter and configured to be translatable within the outer guide catheter, and a delivery catheter positioned radially within the inner sleeve and configured to be translatable within the inner sleeve. In some embodiments, the delivery catheter is configured to enable delivery of an interventional device through the inner sleeve and outer guide catheter to a targeted treatment area within a body.

In some embodiments, the delivery device includes a routing catheter configured to transmit an interventional device to a targeted area within the body, the routing catheter including a catheter wall having one or more routing channels (e.g., lumens, grooves, etc.) extending longitudinally along at least a portion of the routing catheter. The routing channel(s) are configured to position and route respective sensor wires (e.g., pressure wires, FFR wires) with respect to the routing catheter.

Certain embodiments include interventional devices coupled with or associated with one or more sensors to enable monitoring of one or more hemodynamic properties during and/or after deployment of the interventional device. In some embodiments, the interventional device is a fillable spacer configured for placement within a heart valve to provide a surface for coaptation of valve leaflets to minimize or eliminate regurgitation at the valve. In some embodiments, the interventional device is a chord replacement device or a tether (e.g., transapical tether).

In some embodiments, a chord replacement assembly includes an actuator component in the form of an access component. The access component is positioned outside the heart and is configured to enable adjustment of the length of the cord replacement device. In some embodiments, a controller is in communication with the access component to direct automatic tensioning adjustments in response to hemodynamic information received from the one or more sensors. Similarly, in some embodiments, a spacer device assembly includes an actuator component in the form of a fluid port positioned outside the heart. The fluid port is in fluid communication with a fluid reservoir to enable fluid to be directed to the spacer or to receive fluid withdrawn from the spacer. In some embodiments, a controller is configured to direct automatic adjustment of the spacer device in response to hemodynamic information received from the one or more sensors.

In some embodiments, an occluder device configured for occluding a defect (e.g., a septal defect or a defect related to the left atrial appendage) is connected to one or more sensors extending away from the occluder device. A connector joining the occluder device and the one or more sensors is configured in size and shape so as to position the one or more sensors in desired positions within the treatment site for making desired hemodynamic measurements, such as within a potential zone of regurgitant flow above a mitral valve.

In some embodiments, a tissue fixation clip is configured to include one or more attachable sensor mounts, such as a distally extending mount and/or a proximally extending mount. In some embodiments, a distal mount is coupled to a distal side of the clip, and a proximal mount is coupled to a connector extending proximally from a body of the clip. The connector includes a proximal coupling enabling detachable connection of the clip to a delivery catheter and to the proximal mount, such that the proximal mount may be joined to the connector after the clip has been positioned and deployed by the delivery catheter, and after the delivery catheter has been detached and removed.

In some embodiments, an interventional annuloplasty assembly is configured to provide pressure-sensing functionality. An annuloplasty device includes a lumen with a plurality of anchors positionable within the lumen. The plurality of anchors, when deployed within the lumen, function to anchor the annuloplasty device along a plurality of positions. The annuloplasty assembly includes a connecting wire connecting the plurality of anchors such that tensioning of the connecting wire brings the plurality of anchors closer together to tighten the annuloplasty device. One or more sensors are coupled to the connecting wire of the annuloplasty device to enable the measuring of one or more hemodynamic properties at a targeted treatment site upon deployment of the annuloplasty assembly at the targeted treatment site. The position of the sensor(s) on the annuloplasty assembly can be configured during the intervention process (on a specific patient state) such that the sensor(s) enable the interrogation of flow across local regions of the valve that are expected to exhibit persisting or recurrent regurgitation.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 4A-4D illustrate cross-sectional views of various embodiments of guide catheters or sleeves of a delivery device configured with pressure-monitoring functionality;

FIGS. 6A-6D illustrate various embodiments of a delivery device including one or more lumens and/or grooves for routing a sensor wire to a targeted area for measuring pressure at the targeted area;

DETAILED DESCRIPTION

Figure 1A:
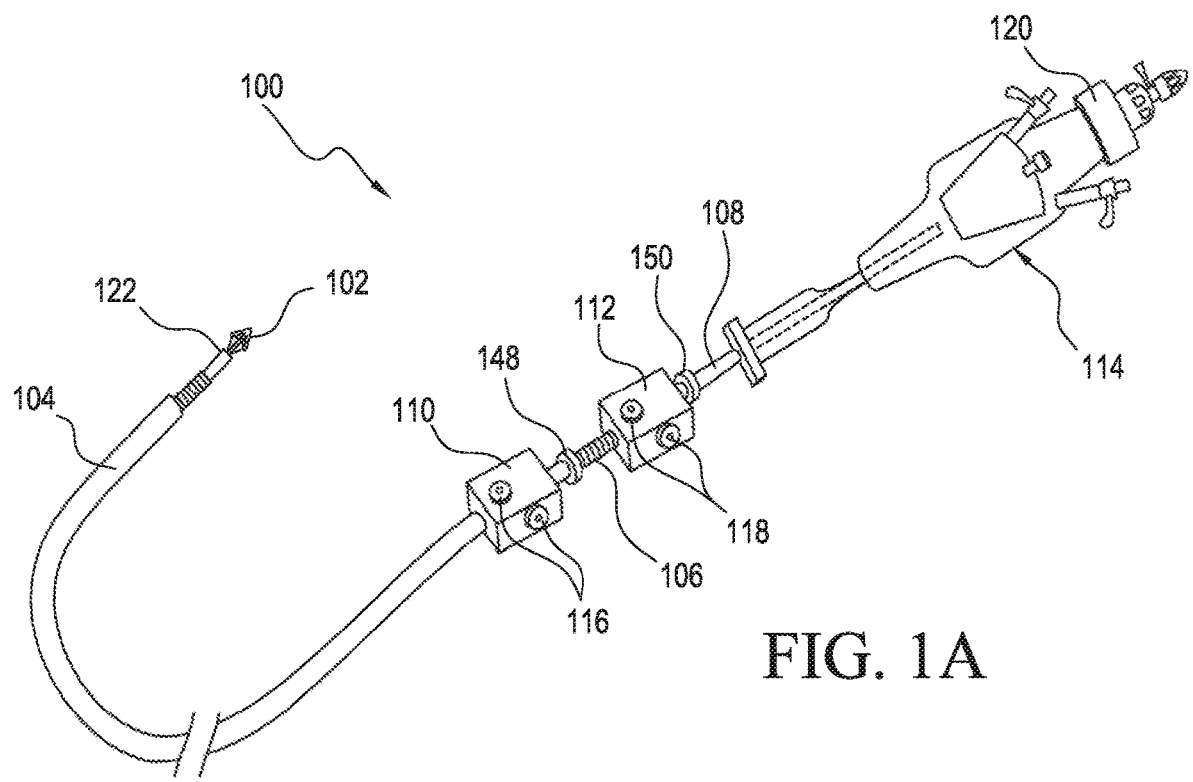
FIGS. 1A and 1B illustrate an exemplary delivery device suitable for use with one or more of the pressure-monitoring components described herein.

Certain embodiments described herein are directed to devices, systems, and methods enabling the intra-procedural monitoring of cardiac pressure and related hemodynamics. In some embodiments, pressure monitoring is enabled before, during, and/or after a cardiac procedure. Although many of the embodiments described herein are described in the context of a mitral valve repair procedure, it will be understood that the related principles and/or components may also be applied within the context of another cardiac procedure, such as a mitral valve replacement, tricuspid valve repair or replacement, chordae tendineae repair or replacement, septal defect repair, occlusion, leaflet modification, leaflet plication, or other cardiac procedure where the monitoring of blood pressure or other hemodynamic properties is desired.

In addition, while certain embodiments are described as enabling "intra-procedural" pressure monitoring, it will be understood that at least some embodiments described herein are configured, additionally or alternatively, to provide post-procedural pressure monitoring. For example, some embodiments described herein are configured to be deployed into or implanted onto or within a patient's heart, and may include pressure-sensing components configured to continue to monitor pressure after deployment and/or implantation.

Further, although several examples are described herein as including one or more components for measuring blood pressure, it will be understood that such pressure monitoring can, alternatively or additionally, include blood flow monitoring and/or the monitoring of other hemodynamic properties. For example, embodiments described as having a pressure wire, pressure catheter, pressure sensor, and/or pressure transducer may, alternatively or additionally, include a flow wire, flow catheter, flow sensor, and/or flow transducer.

Accordingly, the terms "sensor," "sensor wire," "transducer," and the like, as user herein, typically refer to pressure-sensing devices, but in other embodiments, may additionally or alternatively refer to flow sensing devices and/or devices configured for measuring other hemodynamic properties. In addition, although various descriptions make reference to "sensor" in the singular, it will be understood that alternative embodiments include one or more sensor arrays having multiple different sensors arranged together as a sensor array unit.

At least some of the embodiments described herein beneficially enable intra-procedural pressure monitoring during a cardiac procedure while minimizing or overcoming one or more limitations present in prior art devices, systems, and methods. For example, some embodiments minimize or overcome limitations related to one or more of: tangling/snagging due to undesired interactions between pressure-sensing components and other device components, such as catheters, guidewires, replacement valves, deployable components, and/or other components; trauma caused by insertion of a pressure wire or other pressure-sensing device; repeatability of positioning the pressure-sensing device at the location from which pressure is measured; and accuracy of pressure measurements.

Additional benefits that may be provided by one or more of the embodiments described herein include improved reduction in regurgitation after treating a regurgitant heart valve (e.g., mitral valve). For example, continuous monitoring of atrial and/or ventricular pressure during and after a procedure can enable better valve repair, implant placement, and post-operative care, for example, leading to reductions in regurgitation of the treated valve. One or more embodiments can also enable better decision making by the operator and other caretakers. For example, in making procedural decisions such as the number and positioning of implants, operators often rely on echocardiographic imaging. For long, challenging procedures, echo probes may heat up and image resolution correspondingly degrades. Information provided by at least some of the embodiments described herein can aid in the decision-making and reduce an operator's reliance on echocardiographic imagery.

One or more embodiments described herein can also improve decision-making where anatomy and/or hemodynamics are complex, such as where regurgitation jets are eccentric or where a large number of jets exist. One or more embodiments described herein can also reduce reliance on relatively more subjective interpretation of echocardiographic imagery by providing relatively more objective quantitative pressure and/or flow data, which enables the use of easier numeric procedural guidelines for new operators. One or more embodiments described herein also enable improved measuring and understanding of hemodynamic changes that occur throughout a procedure, such as the changes that occur when an implant is in the vicinity of a valve, before, during, and after deployment. One or more embodiments described herein also enables more effective dosing of medication (e.g., norepinephrine) to better counter sedation effects and/or to provide other desired clinical effects.

Some embodiments are directed to an interventional delivery device having one or more components configured to provide pressure-sensing functionality. FIG. 1A illustrates one example of a delivery device 100 suitable for use in conjunction with one or more of the embodiments described herein. The illustrated delivery device 100 is configured as a multi-catheter guiding system for delivering an interventional device 102 to a targeted treatment area (e.g., through transapical, transfemoral, or transthoracic introduction). By way of example, the interventional device 102 can be a replacement valve (e.g., mitral, tricuspid, aortic, or pulmonary valve), tissue fixation device (e.g., valve clip), chordae tendineae (i.e., chord) replacement or repair device, annuloplasty ring, occluding device, septal defect repair device, spacer, suture device, or other interventional device suitable for use in a structural heart procedure.

The illustrated delivery device 100 includes a proximal end 120 and a distal end 122, a guide catheter 104, a sleeve 106 positioned radially within the guide catheter 104, and a delivery catheter 108 positioned radially within the sleeve 106, as shown. The delivery catheter 108 is translatable within the inner sleeve 106, and the inner sleeve 106 is translatable within the outer guide catheter 104.

Manipulation of the guide catheter 104 and/or sleeve 106 enables the interventional device 102 to be directed through a patient's vasculature to a targeted treatment area of the patient's heart. In the illustrated embodiment, angling of the guide catheter 104 and the inner sleeve 106 is achieved using the guide catheter handle 110 and the sleeve handle 112 attached to the proximal ends of the guide catheter 104 and the sleeve 106, respectively. As shown, the guide catheter handle 110 is coupled to the proximal end of the guide catheter 104, and the sleeve handle 112 is coupled to the proximal end of the sleeve 106. The sleeve 106 is inserted through the guide catheter handle 110 to position the sleeve 106 radially within the guide catheter 104. The delivery catheter 108 is inserted through the sleeve handle 112 to position the delivery catheter radially within the sleeve 106 and the guide catheter 104. In some embodiments, a delivery catheter is assembled within a sleeve to limit translation within the sleeve. For example, a delivery catheter may have a larger profile than the sleeve at sections of the delivery catheter proximal and/or distal to the sleeve according to the order of construction/assembly.

The guide catheter 104 and/or the sleeve 106 include steering mechanisms to position the distal ends of the guide catheter 104 and/or sleeve 106 in desired directions. In the illustrated embodiments, the steering mechanisms are provided in the form of steering controls 116 and 118, which are configured as steering knobs for controlling the tensioning of one or more pullwires running the length of the corresponding guide catheter 104 or sleeve 106 (see FIG. 1B and additional description below). Steering may therefore be achieved by adjusting the tension of one or more pullwires to curve the distal end of the guide catheter 104 and/or sleeve 106 in the direction of the tension. Additionally, or alternatively, one or more of the guide catheter 104 or the sleeve 106 may be precurved to provide a desired angling for properly traversing a patient's vasculature in the context of a particular procedural approach.

For example, precurvature or steering of the guide catheter 104 can direct the distal end of the guide catheter 104 to form a first curve, while precurvature or steering of the sleeve 106 can direct the distal end of the sleeve 106 to form a second curve. In a typical implementation, the first curve differs from that of the second curve so that together the curves form a compound curve. Often, at least for a mitral valve procedure using a transfemoral approach, the primary curve has a radius of curvature in the range of 0.8 to 1.0 inches and the secondary curve often has a radius of curvature in the range of 0.050 to 0.750 inches. Advancement of the delivery catheter 108 through the sleeve 106 thereby guides the delivery catheter 108 through the resulting compound curve, and enables the interventional device 102 to be delivered to the targeted treatment area in a desired orientation. The interventional device 102 may then be actuated, deployed, and/or released through manipulation of the delivery handle 114. In some embodiments, a guide catheter can be configured with precurvature and/or steering functionality so as to accommodate transjugular delivery or other vascular delivery. In some embodiments, curvature of both the guide catheter 104 and the sleeve 106 may be oriented in the same direction to provide an even higher angular curvature about a single axis.

As shown, the delivery device 100 also includes hemostatic valves 148 and 150 configured to provide leak-free sealing of the entry points for the sleeve 106 into the guide catheter 104 and the delivery catheter 108 into the sleeve 106, respectively. The hemostatic valves 148 and 150 are also configured to reduce the risk of air introduction and to prevent back bleeding.

Figure 1B:
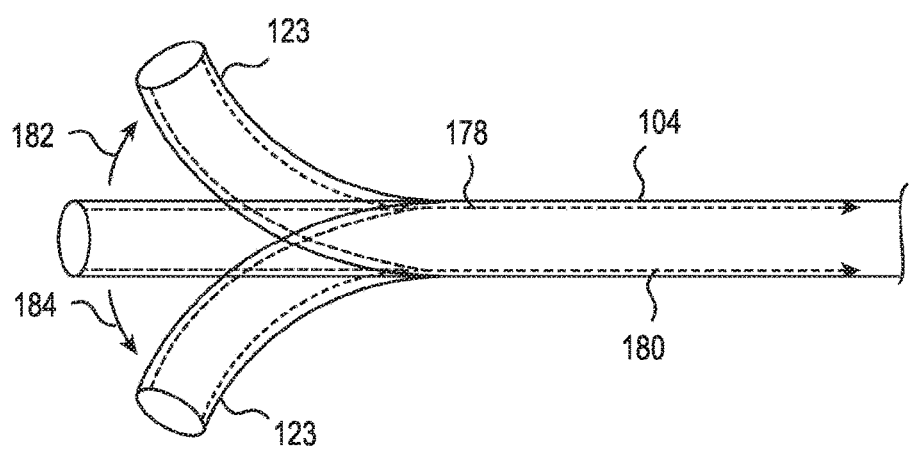

FIG. 1B illustrates an exemplary pullwire-based steering mechanism that may be utilized with one or more of the embodiments described herein. FIG. 1B illustrates a pullwire-based steering mechanism associated with the guide catheter 104; however, similar principles may be applied to the sleeve 106 as well in order to form a steerable sleeve. As shown, the guide catheter 104 includes a first pullwire 178 slidably disposed in a lumen within the wall of the guide catheter 104 and extending to the distal end 123. By applying tension to the pullwire 178 in the proximal direction, the distal end 123 curves in the direction of the pullwire 178 as illustrated by arrow 182. Likewise, placement of a second pullwire 180 along the opposite side of the guide 104 will allow the distal end 123 to be curved in the opposite direction, as illustrated by arrow 184, when tension is applied to the second pullwire 180.

Thus, the opposed pullwires 178 and 180 within the walls of the guide catheter 104 enables the distal end 123 to be steered in opposite directions. This provides a means of correcting or adjusting a curvature. For example, if tension is applied to one pullwire to create a curvature, the curvature may be lessened by applying tension to the diametrically opposite pullwire. The illustrated embodiment includes two opposing pullwires. Other embodiments may include a single pullwire, or may include more than two pullwires. In addition, pullwires and associated lumens may be placed in any arrangement, singly or in pairs, symmetrically or non-symmetrically, to enable desired curvature capabilities. Pullwires may be fixed at any location along the length of the guide catheter 104 by any suitable method, such as gluing, tying, soldering, and the like. When tension is applied to the pullwire, the curvature forms from the point of attachment of the pullwire toward the proximal direction. Typically, however, pullwires are attached near the distal end 123 of the guide catheter 104.

Additional examples and details related to delivery devices for directing an interventional device to a targeted treatment area, including steering systems, fixation devices, valves, handles, and deployment mechanisms, are described in U.S. Pat. No. 7,666,204 and U.S. Patent Application Publication No. 2017/0100250, the disclosures of each of which are incorporated herein in their entirety by this reference.

Figure 2:
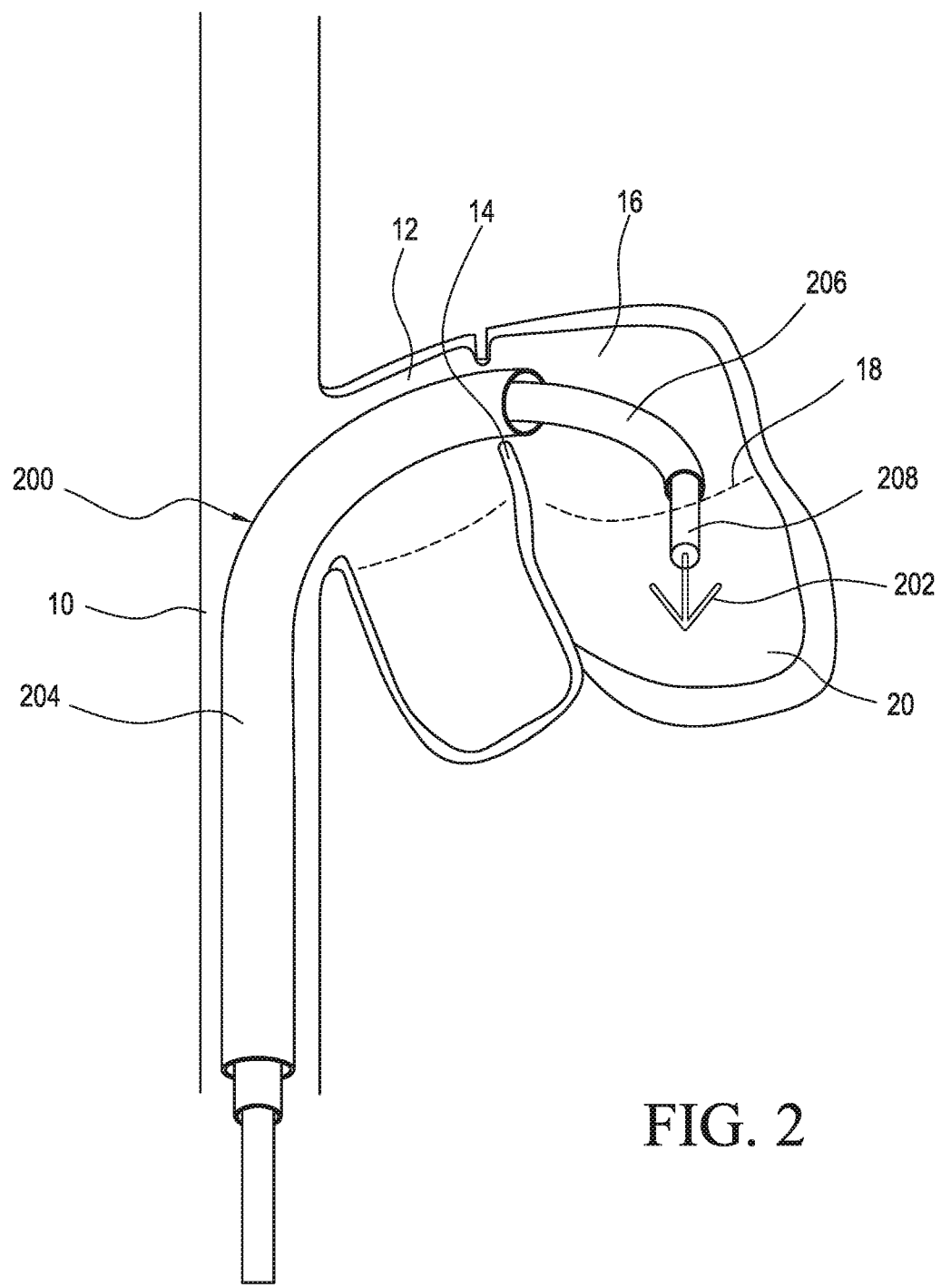
FIG. 2 illustrates a typical transfemoral approach for delivering an interventional device and/or performing an interventional procedure.

FIG. 2 illustrates a transfemoral approach using a delivery device 200 in a procedure requiring access to the left side of the heart, such as a mitral valve repair or replacement procedure. As shown, an interventional device 202 is delivered through the femoral vein by passing a delivery catheter 208, to which the interventional device 202 is coupled, through a guide catheter 204 and a sleeve 206. The interventional device 202 is passed through the inferior vena cava 10, into the right atrium 12, through the inter-atrial septum 14 via a puncture, and into the left atrium 16. When necessary or desired, the interventional device 202 may then be directed across the mitral annulus 18 and into the left ventricle 20 via translation of the delivery catheter 208. As shown, the steering functionality of the guide catheter 204 and/or sleeve 206, combined with the translatability of the sleeve 206 through the guide catheter 204 and the translatability of the delivery catheter 208 through the sleeve 206, enables positioning of the interventional device 202 at the targeted treatment area.

FIGS. 3A-3F illustrate various embodiments of delivery devices configured to enable intra-procedural pressure monitoring. The embodiments shown in FIGS. 3A-3F are illustrated and described in the context of a mitral valve repair procedure following the transfemoral approach described in relation to FIG. 2. However, it will be understood that the elements and principles as described may also be applied to other procedures and approaches, such as those involving valve replacement or other structural heart procedures described herein. In particular, the embodiments illustrated by FIGS. 3A-3F and similar embodiments may be beneficially applied in the context of trans-catheter procedures, such as left atrial appendage closure, stem cell needle injection, ablation, diagnostic, imaging procedures, and other trans-catheter procedures where minimizing injury, device profile, and interference between device components are desired. Additionally, principles described in relation to these and other embodiments described herein enable one or more of improved procedural outcomes and valuable feedback for indicating whether problems or complications have occurred.

Figure 3A:
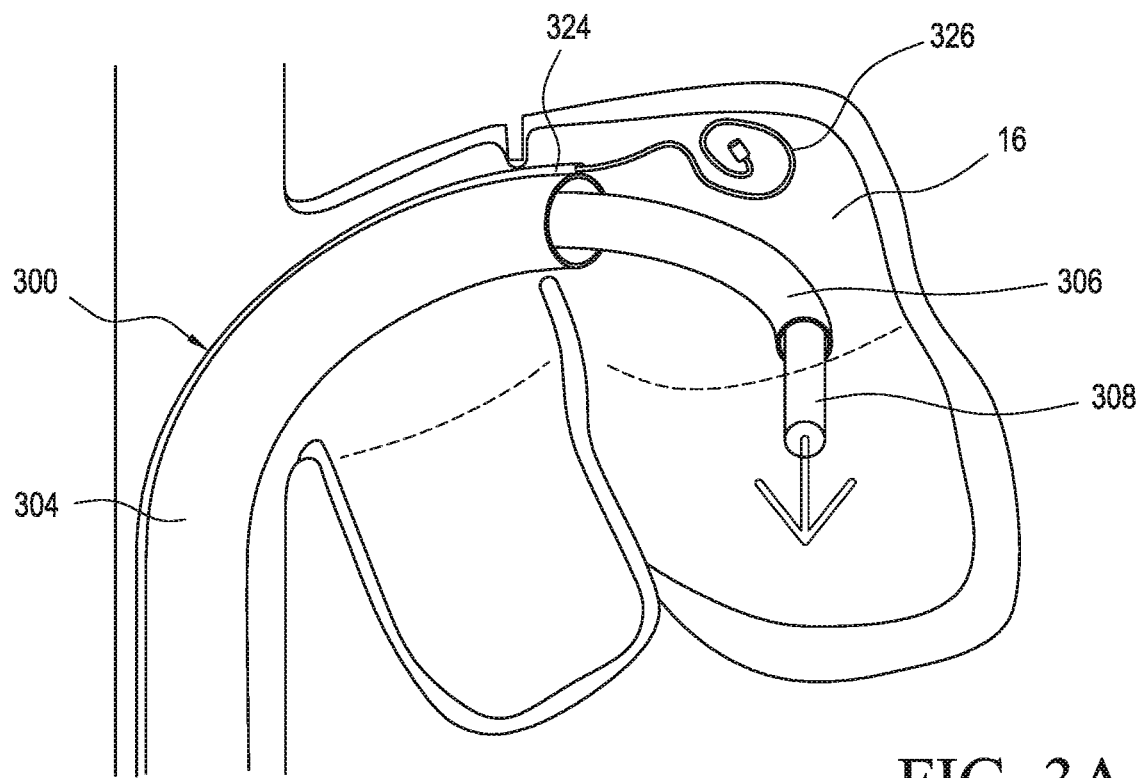
FIGS. 3A-3F illustrate various embodiments of a delivery device including one or more pressure-monitoring components in the context of a mitral valve repair or replacement procedure using a transfemoral approach.

FIG. 3A illustrates an embodiment of a delivery device 300 including a guide catheter 304. In this embodiment, the guide catheter 304 includes a routing lumen 324. As shown, the routing lumen 324 exits into the left atrium 16 such that a sensor wire 326 may be passed through the routing lumen 324 into the left atrium 16 to provide pressure measurements before, during, and/or after the procedure. For example, the illustrated embodiment may be used to position the sensor wire 326 within or near the left pulmonary veins to measure associated pressure.

In preferred embodiments, the sensor wire 326 is shaped (e.g., bent or coiled) so as to be atraumatic in the event of contact with atrial wall tissue or other tissue. The routing lumen 324 preferably has a diameter ranging from about 0.005 to 0.020 inches, or about 0.008 to 0.014 inches, to enable sufficient passage for the sensor wire 326 without inhibiting translation of the sleeve 306 within the guide catheter 304 and without detrimentally affecting the structural integrity of the guide catheter 304.

Figure 3B:
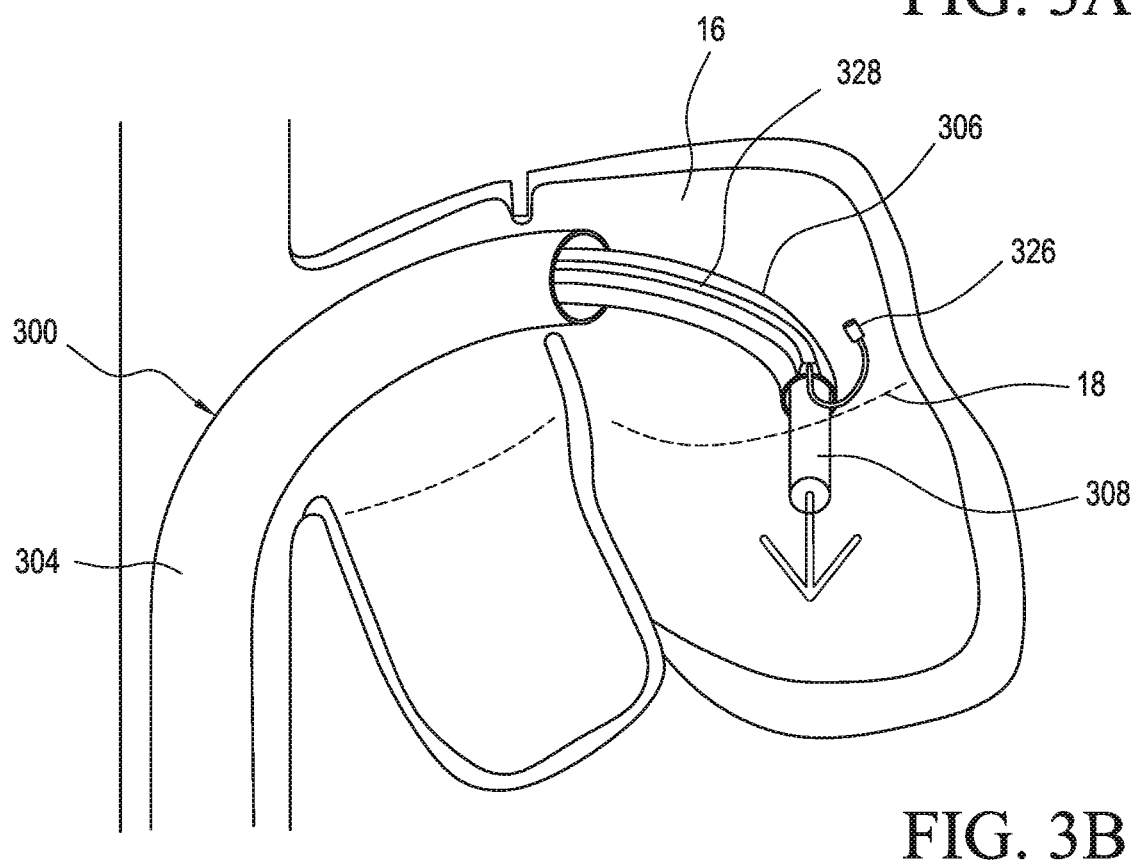

FIG. 3B illustrates an embodiment of the delivery device 300 where the sleeve 306 is configured to include a sleeve routing lumen 328. As shown, the sleeve routing lumen 328 exits into the left atrium 16 near the mitral annulus 18 such that a sensor wire 326 may be passed through the sleeve routing lumen 328 into the left atrium 16 to provide pressure measurements before, during, and/or after the procedure. For example, the illustrated embodiments may be used to position the sensor wire 326 near the mitral valve annulus 18 in order to measure pressure and/or flow in the vicinity of a regurgitant jet due to a defective mitral valve. Because the sleeve 306 is translatable with respect to the guide catheter 304, the illustrated configuration beneficially provides flexibility for repositionable pressure measurements near the vicinity of the mitral valve annulus 18. This is particularly so in embodiments where the sleeve 306 is also configured to be steerable. In some embodiments, the sensor wire 326 is configured with a desired precurvature such that extension of the sensor wire 326 is atraumatic and/or torqueable to enable rotational positioning.

Figure 3C:
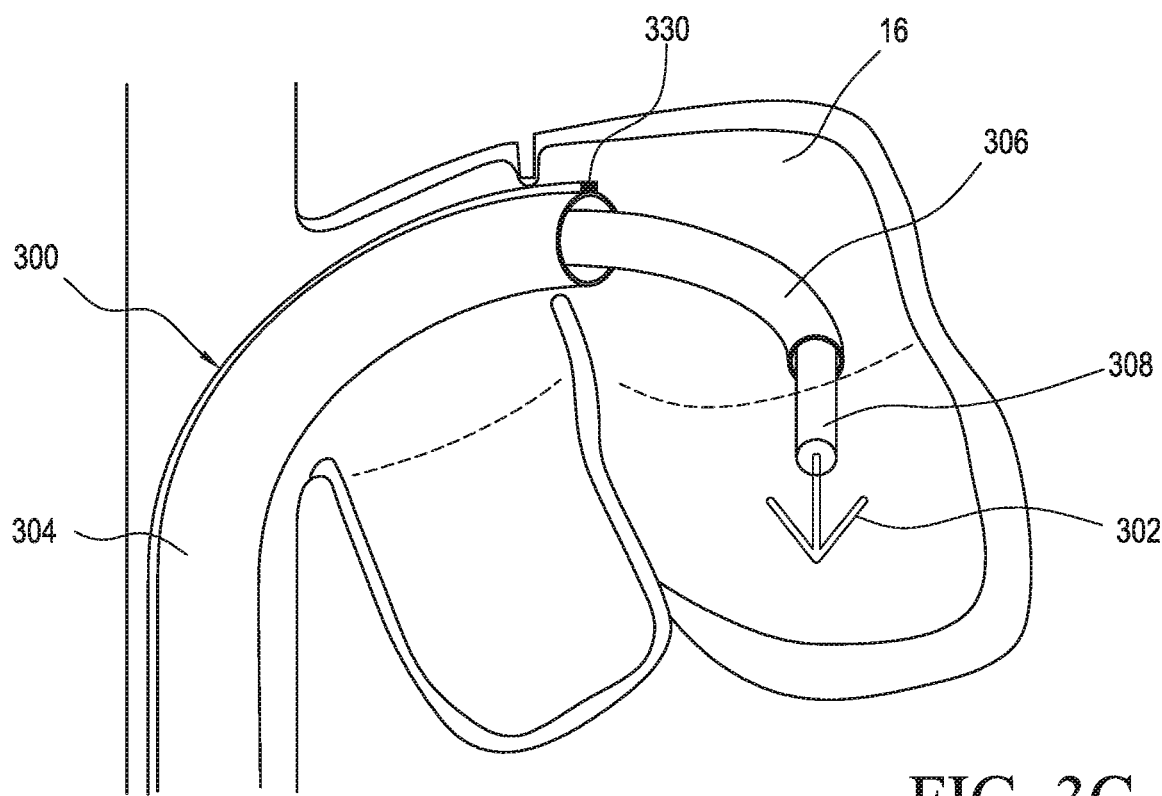

FIG. 3C illustrates an embodiment of the delivery device 300 including a first guide catheter sensor 330 positioned at or near the distal end of the guide catheter 304. As shown, as the distal end of the guide catheter 304 extends into the left atrium 16, the first guide catheter sensor 330 is brought into the left atrium 16 to enable the monitoring of pressure within the left atrium 16. Beneficially, the illustrated configuration provides pressure-monitoring functionality without introducing or extending any components that could undesirably interact with other components of the delivery device 300 (such as tangling with the interventional device 302).

In preferred embodiments, the first guide catheter sensor 330 is configured with a relatively low profile so as to not overly protrude from the outer diameter of the guide catheter 304. In some embodiments, the first guide catheter sensor 330 has a diameter of less than about 3 F (French), or less than about 2 F, or more preferably less than about 1.5 F, such as ranging from about 1 to 1.4 F. Other sensors described herein may be likewise configured.

Figure 3D:
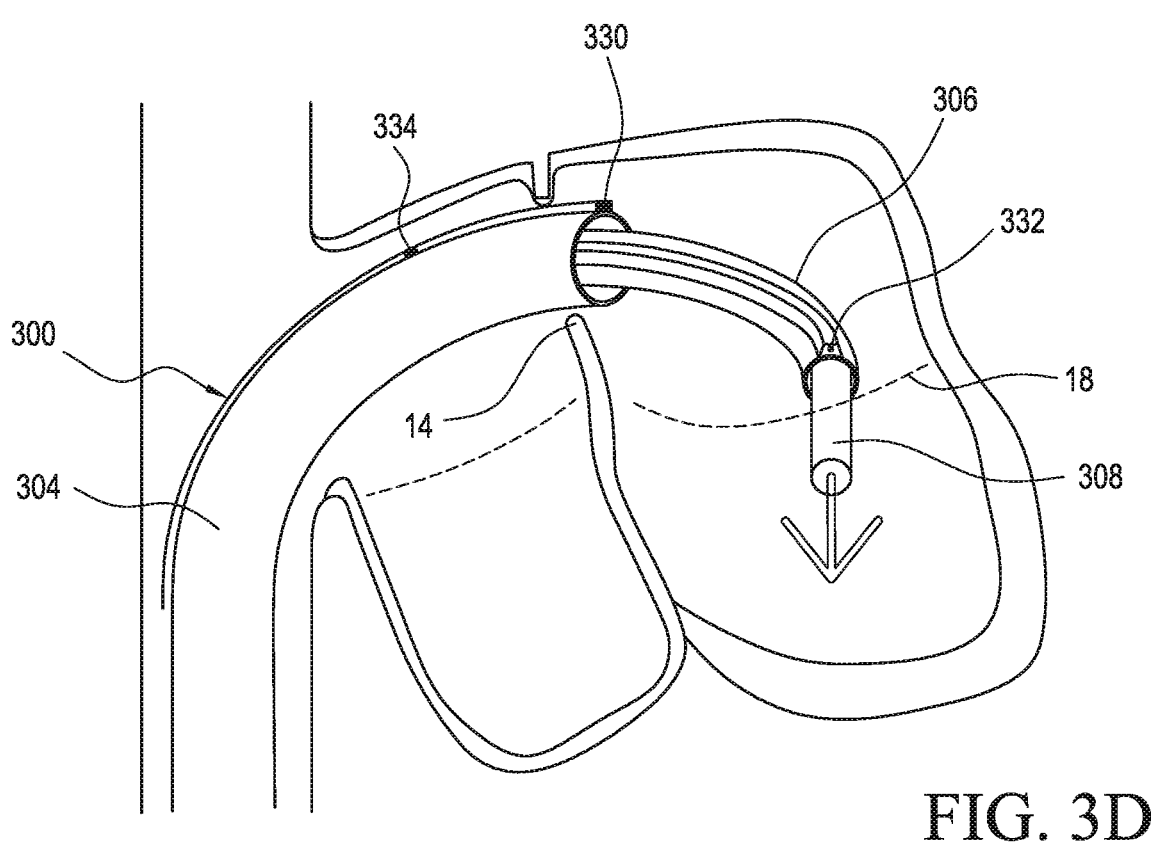

FIG. 3D illustrates an embodiment of the delivery device 300 configured with a sleeve sensor 332 positioned at or near the distal end of the sleeve 306 in the vicinity of the mitral valve annulus 18. Manipulation of the sleeve 306 allows the sleeve sensor 332 to be positioned within a regurgitant jet to provide associated pressure measurements before, during, and/or after deployment of the interventional device 302. The translatability and steerability of the sleeve 306 advantageously provides flexibility for positioning the sleeve sensor 332 in a desired location.

FIG. 3D also illustrates the use of additional sensors. The illustrated embodiment includes, in addition to the sleeve sensor 332, a first guide catheter sensor 330, and a second guide catheter sensor 334 disposed proximally from the first guide catheter sensor 330. As shown, one or more sensors may be positioned along the guide catheter 304 and/or sleeve 306 at multiple locations in order to provide pressure measurements at various anatomical locations without substantially affecting the profile of the delivery device 300. For example, the illustrated embodiment is configured with a sensor arrangement capable of providing real-time pressure measurements at related to one or more of right atrium pressure (e.g., from the second guide catheter sensor 334), left atrium pressure (e.g., from the first guide catheter sensor 330), or regurgitant jet pressure (e.g., from the sleeve sensor 332). One beneficial implementation of the illustrated multiple sensor configuration includes monitoring for leakage across the septum 14 during the procedure. In this and in other embodiments, pressure sensors may be positioned in a circumferential array about one or more of the guide catheter 304, sleeve 306, or delivery catheter 308. Such a sensor configuration can provide feedback enabling optimal device positioning and/or rotational orientation.

Figure 3E:
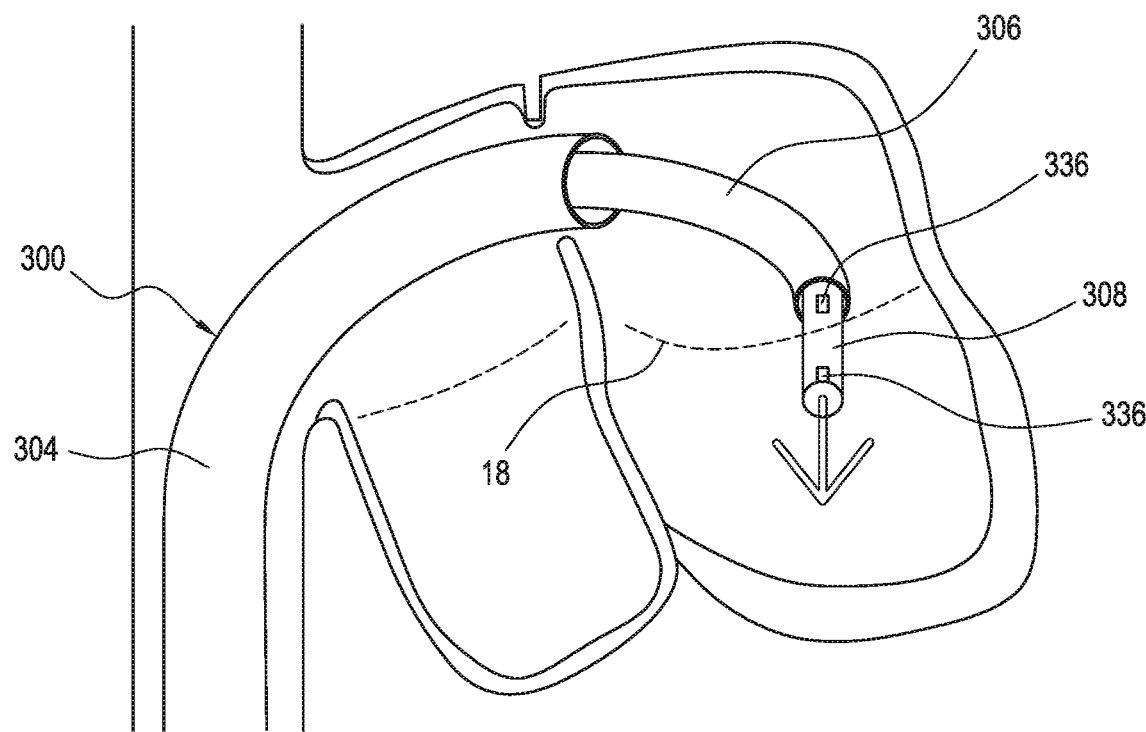

FIG. 3E illustrates an embodiment of the delivery device 300 where the delivery catheter 308 is configured to include one or more delivery catheter sensors 336. As shown, the delivery catheter sensors 336 are disposed at or near the distal section of the delivery catheter 308 that extends out of the sleeve 306 during a typical procedure for deploying the interventional device 302. The positioning of the one or more delivery catheter sensors 336 may be controlled by steering the sleeve 306 and/or by translating the delivery catheter 308 relative to the sleeve 306 and the guide catheter 304. In the illustrated embodiment, two delivery catheter sensors 336 are included such that one is on each side of the mitral valve annulus 18 after extension of the delivery catheter 308. Such a configuration beneficially enables the monitoring of pressure gradients across the mitral valve.

Figure 3F:
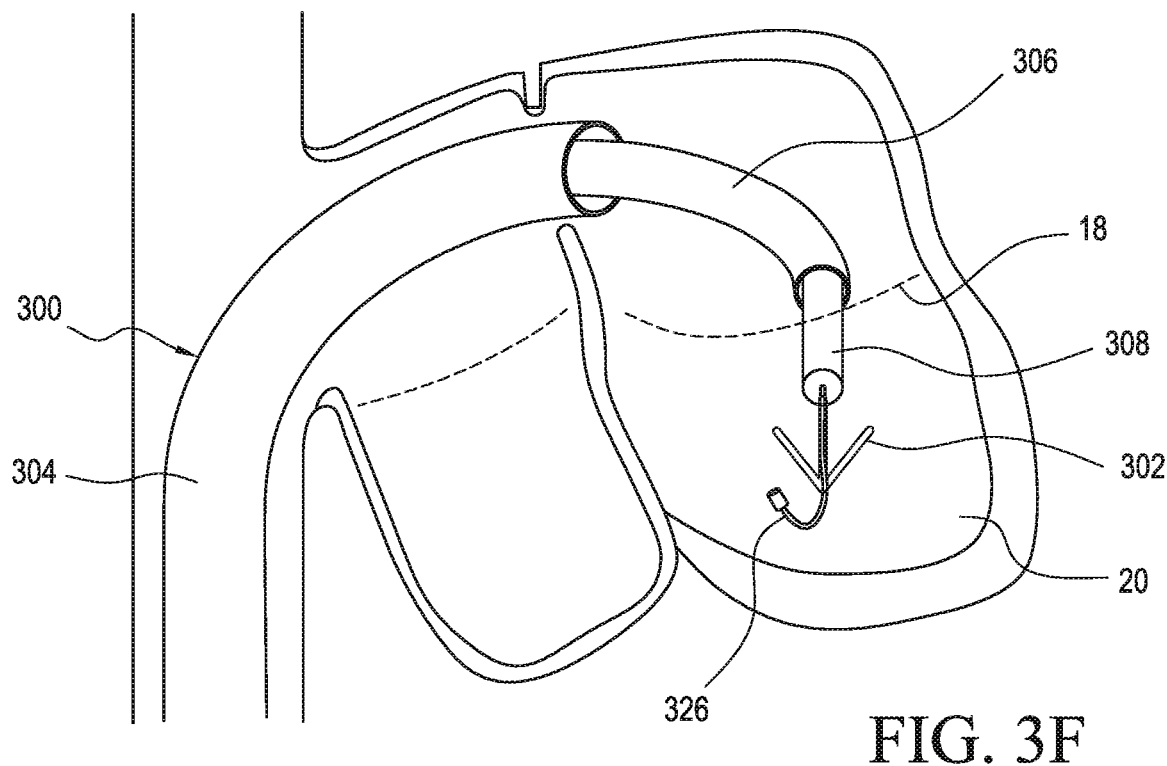

FIG. 3F illustrates an embodiment of the delivery device 300 where a sensor wire 326 is routed through the delivery catheter 308 so as to extend into the left ventricle 20 to provide associated pressure measurements. In some embodiments, the sensor wire 326 is passed through a central axis of the interventional device 302. For example, where the interventional device 302 is a tissue clip, the sensor wire 326 may provide left ventricle pressure readings before and during deployment of the clip. After clipping is complete, the sensor wire 326 may be pulled back through the central axis of the clip and through the repaired mitral valve annulus 18.

Some embodiments may combine one or more of the components shown in FIGS. 3A-3F. For example, some embodiments may include a plurality of sensors coupled to one or more of the delivery catheter 308, the sleeve 306, or the guide catheter 304. Further, one or more sensors may be utilized in combination with one or more sensor wires routed through or coupled to the delivery catheter 308, the sleeve 306, or the guide catheter 304.

FIGS. 4A-4C illustrate cross-sectional views of different embodiments of guide catheters or sleeves suitable for use in housing and routing one or more sensor wires and/or sensors from a proximal end of a delivery device toward a distal end. The following examples are directed to embodiments of guide catheters. However, it will be understood that the examples may also apply to inner sleeves configured to house and route one or more sensor wires and/or sensors.

FIGS. 4A-4C illustrate various configurations of a guide catheter 404 including one or more lumens longitudinally disposed through the wall of the guide catheter 404. The configurations illustrated in FIGS. 4A-4C may represent separate exemplary embodiments or may represent different sections combinable into a guide catheter of one or more such sections. One or more of the embodiments illustrated in FIGS. 4A-4C may be utilized as a guide catheter and/or sleeve in the embodiments shown in FIGS. 3A-3F, or in other delivery device embodiments described herein.

The guide catheter 404 may be formed of one or more of a variety of materials along one or more segments or layers. Example materials include polyurethane, polyether block amides (e.g., as sold under the trade name Pebax®), nylon, polyester, polyethylene, polyimide, polyethylenetelephthalate (PET), polyetheretherketone (PEEK), and combinations thereof. In addition, the walls of the guide catheter 404 may be reinforced with a variety of structures, such as metal braids or coils. Such reinforcements may be along the entire length of the catheter 404 or in various segments.

FIG. 4A illustrates a guide catheter 404 configured with a plurality of lumens longitudinally disposed within a wall 442 of the guide catheter 404. In one example, occupied lumens 438 are used to house and route pullwires and/or other components of the delivery device. As shown, the guide catheter 404 includes additional lumens 440 that are configurable as routing lumens to house and route a sensor wire, sensor, or catheter. In preferred embodiments, a routing lumen is configured as less than about 2 F, more preferably less than about 1.5 F, such as about 1 to 1.5 F, in order to accommodate the pressure-sensing device while maintaining sufficient structural integrity of the wall 442 and to avoid hindering the translation of other components disposed within the guide catheter 404 (such as a steerable sleeve and/or delivery catheter). Likewise, the thickness of the wall 442 is preferably about 0.0150 to 0.0300 inches, or about 0.0200 to 0.0250 inches, or about 0.0225 inches.

FIG. 4B illustrates another configuration of the guide catheter 404. In some embodiments, FIG. 4A represents a more proximal section of the guide catheter 404 while FIG. 4B represents a more distal section of the same guide catheter 404. As shown, the wall 442 includes a plurality of occupied lumens 438 and an additional lumen 440. The additional lumen 440 may be configured as a routing lumen to house and route a pressure-sensing device. In embodiments where FIGS. 4A and 4B represent different sections of the same guide catheter 404, the additional lumen 440 is aligned so as to run the length of at least a portion of each section as a continuous lumen.

FIG. 4C illustrates an embodiment of the guide catheter 404 including an enlarged lumen 444 configured to provide passage of a pressure-sensing device. In some embodiments, the enlarged lumen 444 is formed with an ovoid shape having a major axis that is tangential to circumference of the guide catheter 404 and a minor axis that is transverse to the circumference of the guide catheter 404. In some embodiments, the major axis ranges from about 0.014 to 0.026 inches, or about 0.018 to about 0.022 inches, while the minor axis ranges from about 0.012 to 0.020 inches, or about 0.014 to 0.018 inches. In at least some circumstances, the ovoid shape of the enlarged lumen 444 beneficially provides sufficient clearance for the profile of a pressure-sensing device to pass while minimizing reductions in wall thickness of the guide catheter.

The embodiment shown in FIG. 4C may also represent a ring structure coupled to the distal end of a guide catheter configured to anchor one or more pull wires to the distal end of the guide catheter. In such embodiments, the occupied lumens 438 may be used to attach and anchor one or more pull wires, while the enlarged lumen 444 allows passage of a pressure-sensing device distally beyond the guide catheter and the ring structure.

FIG. 4D illustrates another embodiment of the guide catheter 404 having a keying mechanism for maintaining a rotational relationship with one or more inner components. For example, the notches 446 of the guide catheter 404 may be configured to match and align with corresponding extensions of a sleeve (not shown) aligned within the guide catheter 404 so as to lock the rotation of the sleeve and the guide catheter 404. As shown, the guide catheter 404 includes an additional lumen 440 configured to route a pressure-sensing device through at least a portion of the guide catheter 404.

Alternative embodiments include inverse keying mechanisms. For example, a guide catheter may include one or more extensions configured to match and align with corresponding notches, grooves, or channels of a sleeve. In some embodiments, notches and corresponding extensions are longitudinally straight so as to align with the longitudinal axis of the respective catheter or sleeve. Alternatively, some embodiments include helically oriented notches and corresponding extensions (e.g., formed through a twisted extrusion process). Such embodiments may operate to improve the reliability of passing one or more sensor wires through a curved conduit structure even in circumstances of severe applied curvatures.

The illustrated notches 446 are asymmetrically radially spaced within the guide catheter 404, such that for at least one of the notches 446, a first neighboring notch is positioned radially closer than a second neighboring notch. Such a configuration beneficially allows room for the additional lumen 440 while also maintaining the keying functionality for locking rotation of the guide catheter 404 to one or more corresponding internal components.

For example, a guide catheter having four equally radially spaced notches (i.e., spaced every 90 degrees) will provide sufficient keying functionality but will have limited space within the wall 442 for placement of an additional lumen 440, at least without risking the structural integrity of the catheter because of the proximity of the lumen to one or more of the notches. In contrast, the illustrated guide catheter 404, which includes three asymmetrically radially positioned notches 446 (e.g., 90, 90, and 180 degrees apart, as shown), provides sufficient space for an additional lumen 440, while the asymmetrically aligned notches 446 still maintain sufficient keying functionality. In this manner, uniform bending stiffness is achieved about all potential bend axes.

The shape of one or more of the additional lumens 440 as shown in FIGS. 4A-4C may be circular in cross-section, ovoid, or may have another cross-sectional shape customized to a particular pressure-sensing device.

Figure 5A:
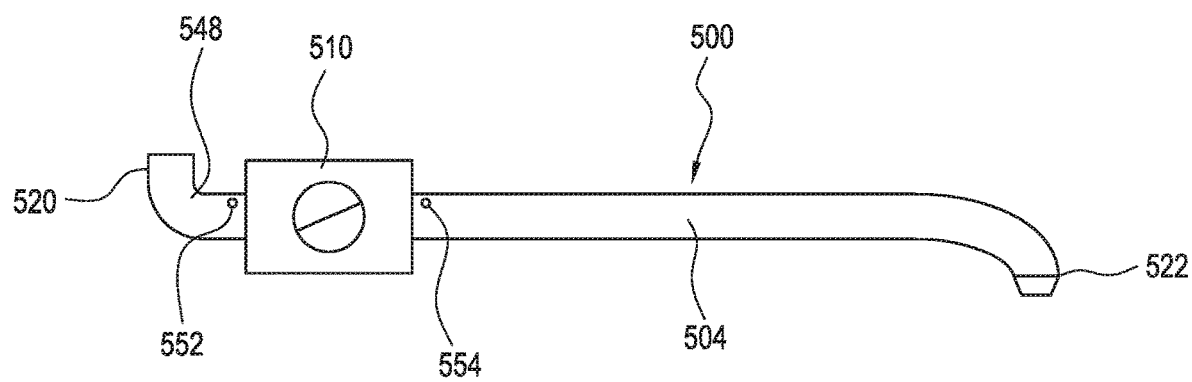
FIGS. 5A and 5B illustrate an embodiment of a delivery device showing exemplary proximal and distal exit points for a sensor wire.
Figure 5B:
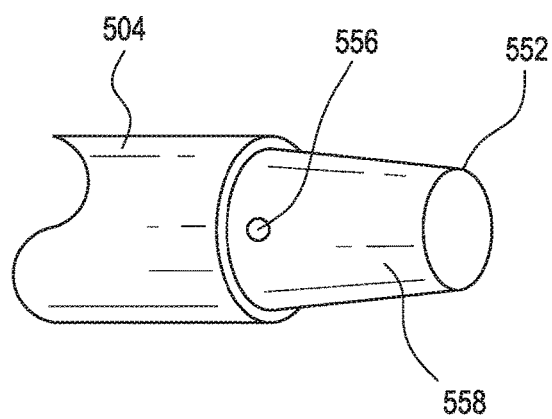

FIGS. 5A and 5B illustrate an embodiment of a delivery device 500 configured to provide intra-procedural pressure monitoring, showing exemplary distal and proximal exit points for a pressure-sensing component of the delivery device 500. As shown, the delivery device 500 includes a proximal end 520 and a distal end 522, a handle 510 with a valve 548 coupled proximally to the handle 510, and a guide catheter 504 extending distally from the handle 510. The delivery device 500 includes a valve proximal exit point 552, a catheter proximal exit point 554, and a distal exit point 556.

As shown in FIG. 5B, the guide catheter 504 includes a soft tip 558 upon which the distal exit point 556 may be positioned. In other embodiments, a distal exit point may be positioned elsewhere on the delivery device 500, such as at a distal section of the guide catheter 504. A pressure-sensing device (such as a sensor wire/catheter) is routable through the device by passing through either the valve proximal exit point 552 or the catheter proximal exit point 554, and passing out of the distal exit point 556.

The embodiment shown in FIGS. 5A and 5B may also be used in a procedure that utilizes at least the distal exit point 556 to advance the guide catheter 504 over a previously positioned sensor wire. For example, some embodiments include the steps of directing a guidewire to the heart transfemorally and crossing the septum to position the guidewire within the left atrium, similarly directing a sensor wire transfemorally and crossing the septum to position the sensor wire within the left atrium, threading the guide catheter 504 over the sensor wire via the distal exit point 556 and using the pre-positioned sensor wire to position the distal end of the guide catheter 504 within the left atrium, and passing the proximal end of the sensor wire out of a proximal exit point to enable pressure monitoring using the sensor wire.

In some embodiments, an interior lumen extending between the catheter distal exit point 556 and a proximal exit point (e.g., the catheter proximal exit point 554 or the valve proximal exit point 552) is configured to function as the pressure-sensing device. For example, a sensor may be coupled to the proximal exit point, where it is in fluid communication with fluid at the distal exit point 556 via the interior lumen such that blood pressure at the distal exit point 556 is transmitted to the proximal exit point where it may be measured. Such an embodiment beneficially limits the need for a sensor wire to be routed through the interior lumen. Further, positioning of the delivery device 500 with respect to a patient can be manipulated to avoid and/or compensate for pressure/head loss.

Figure 6D:
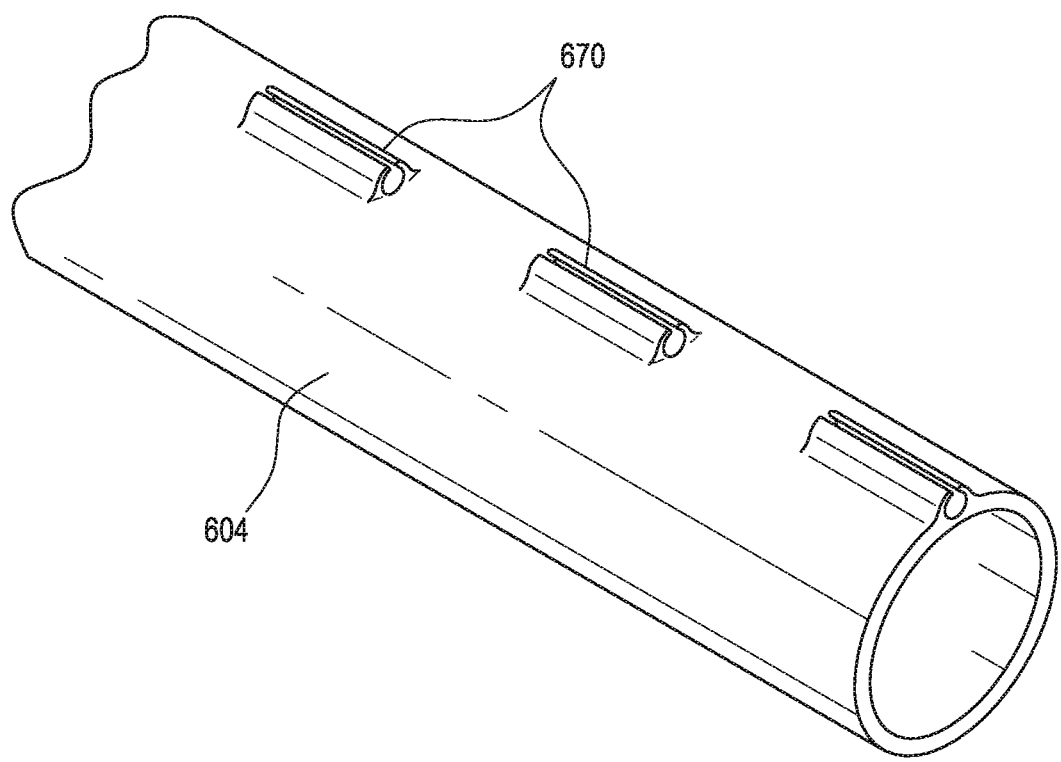

FIGS. 6A-6D illustrate different embodiments useful for associating a sensor wire with a guide catheter 604. FIG. 6A illustrates an enclosed routing lumen 624 formed at an area 660 of extended wall thickness such that the guide catheter 604 includes a raised surface in proximity to the routing lumen 624. FIG. 6B illustrates an alternative embodiment in which the guide catheter 604 includes an open groove 662 configured to receive a sensor wire.

FIG. 6C illustrates another embodiment in which the guide catheter 604 includes an enclosing groove 664 configured to receive a sensor wire and to maintain the position of the sensor wire within the enclosing groove 664. For example, the guide catheter 604 may be formed from a material with sufficient flexibility to allow the extending sections 668 of the catheter to function as tabs, such that as a sensor wire is pressed radially inward toward the enclosing groove 664, the extending sections 668 flex to allow insertion of the sensor wire. Likewise, the extending sections 668 are configured to flex outwardly to allow removal of the sensor wire from the enclosing groove 664 upon outward radial pulling of the sensor wire. The extending sections 668 are preferably formed from a soft, atraumatic material such as a polyether block amide (e.g., Pebax®), or a soft elastomeric material enabling insertion and removal of the sensing wire.

FIG. 6D illustrates another embodiment in which the guide catheter 604 includes one or more clips 670 configured to receive a sensor wire and maintain the position of the sensor wire relative to the guide catheter 604. The embodiment shown in FIG. 6D may be similar to the embodiment of FIG. 6C but with the clips 670 being disposed on discrete sections of the guide catheter 604 rather than forming a continuous groove along the length of the guide catheter 604. Such embodiments beneficially allow rapid and easy coupling and decoupling of a sensor wire to the guide catheter 604.

The embodiments illustrated in FIGS. 6A-6D beneficially enable one or more sensor wires to be associated with the guide catheter 604 while allowing the one or more sensor wires to rotate and translate relative to the guide catheter 604. In some embodiments, a guide catheter includes a combination of the configurations shown by FIGS. 6A-6D. For example, some embodiments may include separate sections having different groove and/or routing lumen configurations.

The embodiments illustrated in FIGS. 6A-6D include single lumens or grooves. Other embodiments of guide catheters or sleeves may include multiple lumens and/or grooves. For example, some embodiments may include, for a given longitudinal section of a guide catheter or sleeve, a first groove and a second groove positioned opposite the first groove, in order to provide one or more of structural stability, structural balance, or easier catheter bending, for example. Groove axes may be oriented to be substantially coaxial with the catheter axis, as in the illustrated embodiments. Alternatively, one or more grooves may be oriented helically or in another position to optimize functionality for an expected or known curvature of the catheter.

Figure 7:
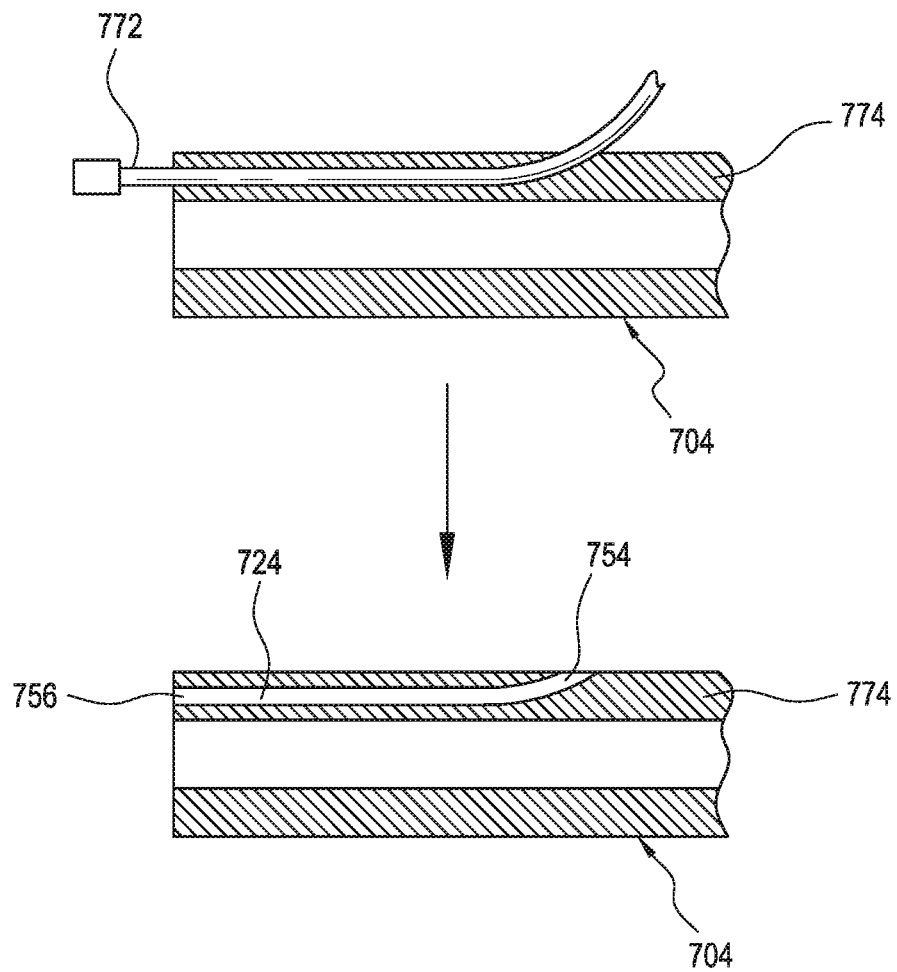
FIG. 7 illustrates an exemplary method for forming a routing lumen in a guide catheter or sleeve of a delivery device.

FIG. 7 illustrates a method by which a groove or a routing lumen may be formed in a guide catheter. As shown, a mandrel 772 may be positioned on a catheter core. During a jacketing process, a jacket thickness 774 is formed so as to sufficiently cover the mandrel 772 (e.g., to form a lumen) or partially cover the mandrel (e.g., to form a groove). Subsequently, the mandrel 772 may be removed, leaving the lumen or groove upon the guide catheter 704. In the illustrated example, the jacket thickness 774 is formed to cover the mandrel 772 so as to result in a routing lumen 724 upon removal of the mandrel 772. As shown, the mandrel 772 is also prepositioned so that removal results in a proximal exit point 754 and a distal exit point 756 for the routing lumen 724. In some embodiments, the mandrel 772 is hollow. A hollow mandrel may remain in the structure of the guide catheter 704 after jacketing to function as a routing lumen. The hollow mandrel may be selected to provide an interior surface with a smoothness greater than the jacketing material and/or may include a surface treatment (e.g., a lubricious coating).

Figure 8A:
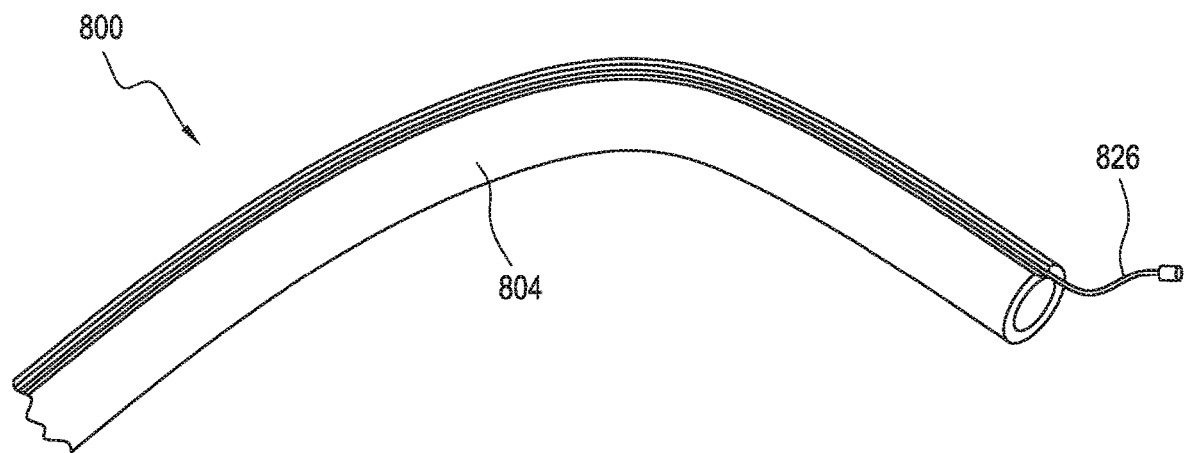
FIGS. 8A and 8B illustrate embodiments of delivery devices showing exemplary sensor wire routing configurations.
Figure 8B:
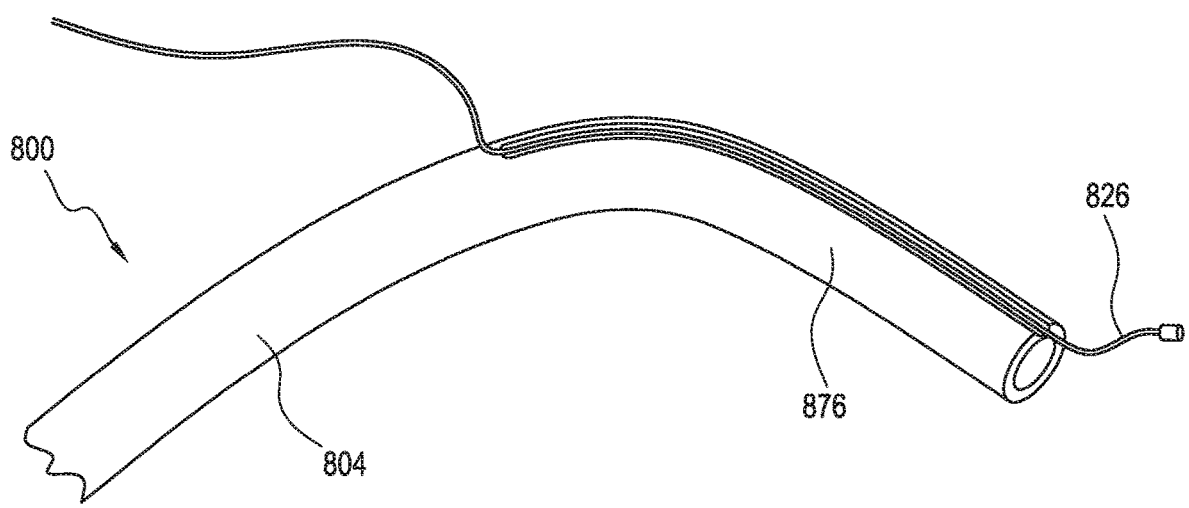

FIGS. 8A and 8B illustrate an embodiment of a delivery device 800 having different sensor wire routing configurations. As shown in FIG. 8A, a sensor wire 826 is routed through substantially the entire length of the guide catheter 804. In an alternative embodiment, the sensor wire 826 is routed through a relatively more limited distal section 876 of the guide catheter 804. Such an embodiment beneficially enables rapid loading and unloading of the sensor wire 826 from the guide catheter 804, particularly in embodiments having grooved receiving areas as opposed to an enclosed routing lumen. However, in other circumstances, a fully enclosed routing lumen may beneficially reduce the risk of decoupling of a sensor wire from a guide catheter. In some embodiments, the distal section 876 includes the most distal 5-50%, or the most distal 10-30% of the guide catheter 804.

Figure 9:
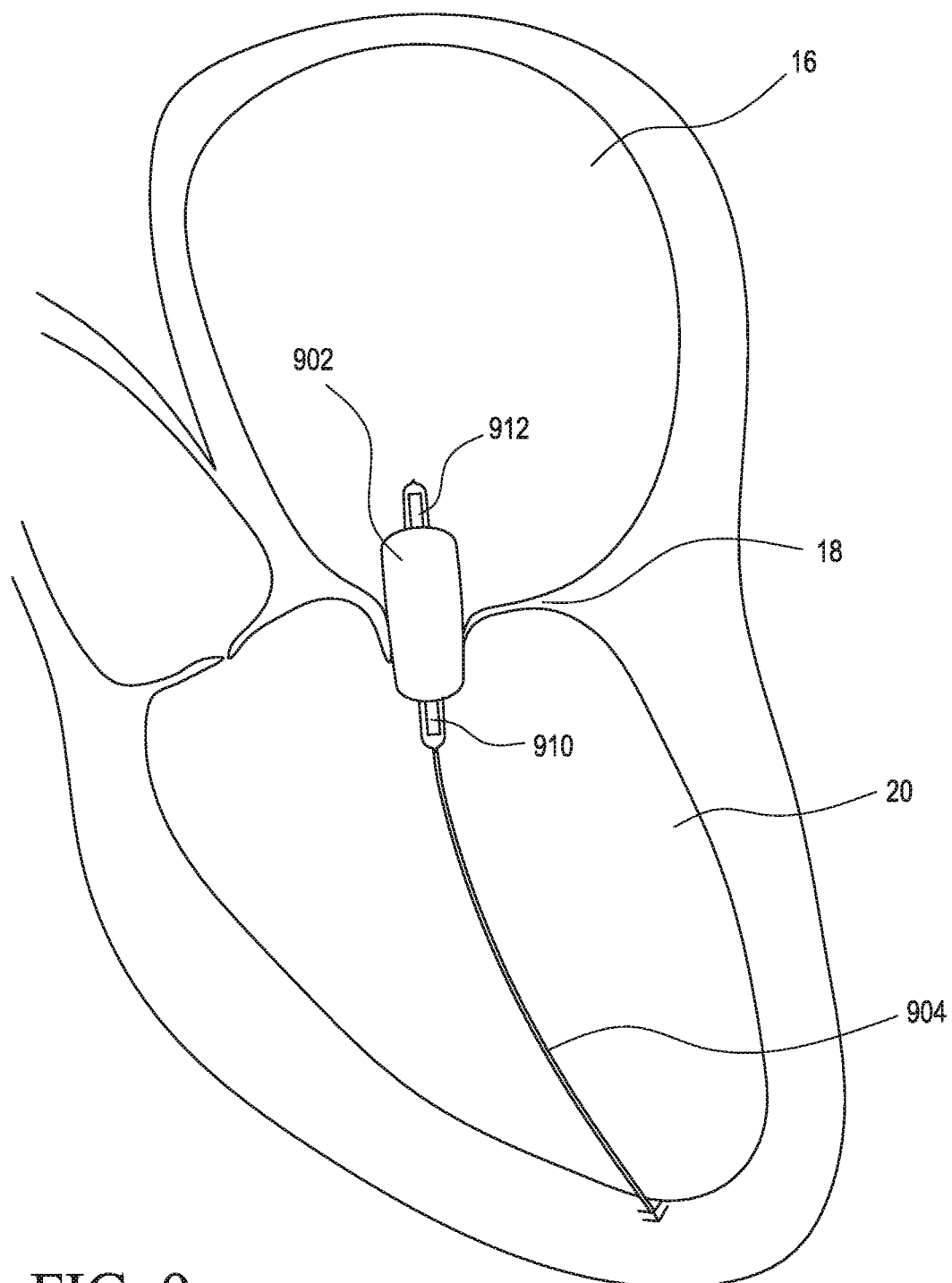
FIG. 9 illustrates an embodiment of a spacer device configured to provide pressure-monitoring.

FIG. 9 illustrates an embodiment of a deployed spacer device 902 configured to provide intra-procedural and post-procedural pressure monitoring. The illustrated spacer 902 is a balloon-like structure (e.g., fluid, gel, or foam filled) that may be positioned across the mitral valve annulus 18 to provide a surface for the mitral valve leaflets to seal against. As a result, the spacer occupies the space of the problematic regurgitant jet, and mitral valve regurgitation is reduced or eliminated. The illustrated spacer 902 includes an anchoring wire 904 (e.g., formed from nitinol, stainless steel, titanium, or other biocompatible material) configured to be fixed into the myocardium of the left ventricle 20 to properly align the spacer 902 with the mitral valve annulus 18, as shown. In some embodiments, the anchoring wire 904 is a remnant of a trackwire utilized to guide the spacer 902 to the mitral valve annulus 18 (see related embodiments in FIGS. 10A-11D and corresponding description). In other embodiments, the spacer 902 is integrally joined to the anchoring wire 904 (e.g., to be delivered or deployed together). Although the anchoring wire 904 and associated trackwire structures are referred to herein as "wires," it will be understood that this term includes rods, shafts, and other such structures suitable for anchoring and/or guiding a spacer.

In some embodiments, the spacer 902 has a substantially circular cross-sectional shape, as illustrated. In other embodiments, a spacer may taper distally or proximally, may have one or more relatively enlarged sections, and/or have non-circular cross-sectional shape, for example. In some embodiments, the anchoring wire 904 is configured to be attachable to or embeddable within the myocardium by including a barbed or fish hook-like distal end configured to resist proximal movement after positioning within the myocardium. Other embodiments may additionally or alternatively include a helically coiled (e.g., corkscrewed) end structure for screwing into the myocardium, one or more suture linkages, or other structures enabling anchoring of the anchor wire 904 to the myocardium so as to position the spacer 902. The illustrated embodiment includes a single anchoring wire 904. Other embodiments may include a plurality of anchoring wires and/or other anchoring structures. The spacer 902, anchoring wire 904, and other components are preferably formed from biocompatible materials. For example, the spacer 902 may be formed from one or more biocompatible and flexible polymers, such as silicone, polyurethane, and the like.

The illustrated spacer 902 also includes a first sensor 910 disposed on a ventricular side of the deployed spacer 902 to measure pressure within the left ventricle 20, and a second sensor 912 disposed on an atrial side of the deployed spacer 902 to measure pressure within the left atrium 16. Embodiments utilizing at least one sensor on either side of the mitral valve annulus 18 beneficially enable the monitoring of pressure gradients across the mitral valve annulus 18. As explained in further detail below, one or more of the sensors 910 and 912 may be integrally joined to the spacer 902 such that they are deployed alongside deployment of the spacer 902, or one or more may be attached to an already deployed spacer device.

Figure 10A:
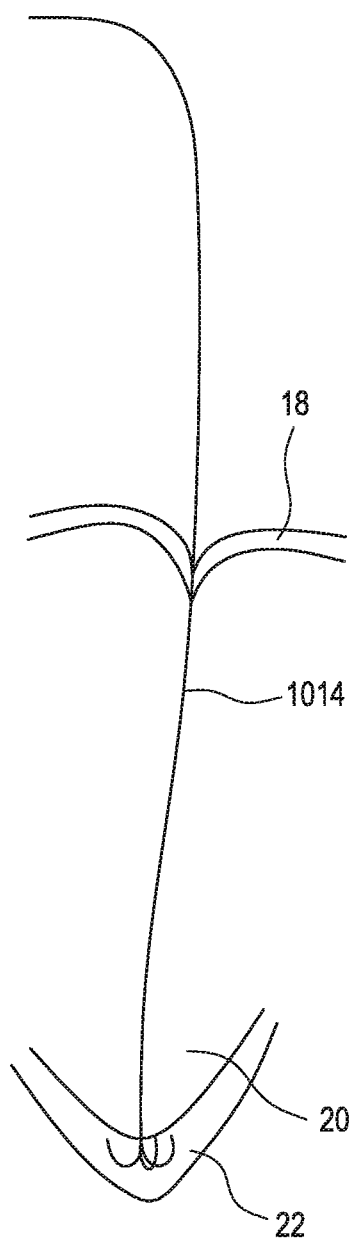
FIGS. 10A and 10B illustrate a procedure for deploying a spacer device having integrally attached sensors.
Figure 10B:
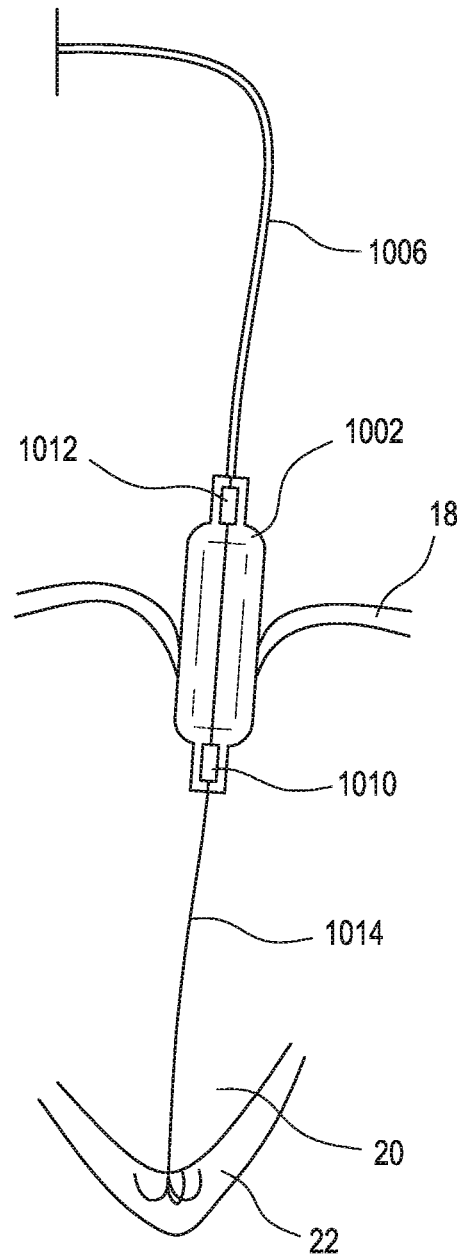

FIGS. 10A and 10B illustrate a deployment procedure, from a transfemoral approach, for a spacer 1002 having integrally attached sensors. FIGS. 11A-11D illustrate a deployment procedure, from a transfemoral approach, for a spacer and sensor system where the sensors 1110 and 1112 are decoupled from the spacer 1102 as separate elements. The embodiment shown in FIGS. 10A and 10B and 11A-11D may utilize or include one or more features or components of the embodiment illustrated in FIG. 9, and the description related to FIG. 9 is therefore incorporated herein to the description related to FIGS. 10A and 10B and 11A-11D, and vice versa.

As shown in FIG. 10A, a trackwire 1014 is directed across the mitral valve annulus 18 into the left ventricle 20 where it is anchored into the myocardium 22 (e.g., at the apex of the left ventricle 20). As described above in relation to FIG. 9, the anchoring may be accomplished through use of a barbed structure, corkscrew structure, and/or other anchoring structure. In some embodiments, the trackwire 1014 is configured to be flexible along the entirety of its length. In other embodiments, the trackwire 1014 may have one or more relatively more rigid sections. For example, some embodiments may include a distal section having a relatively greater rigidity, to aid in anchoring, than more proximal sections of the trackwire 1014.

As shown in FIG. 10B, a spacer 1002 is subsequently directed into the mitral valve annulus 18 via a delivery catheter 1006 as guided by the trackwire 1014. Once properly positioned, the delivery catheter 1006 may be decoupled from the spacer 1002. The sensors 1010 and 1012 provide feedback enabling optimal positioning of the spacer 1002 within the mitral valve annulus 18. For example, real-time feedback provided by the sensors 1010 and 1012 during a procedure can allow an operator to properly position the spacer 1002 prior to decoupling from the delivery catheter 1006.

In some embodiments, the spacer 1002 is translatably coupled to the trackwire 1014. For example, the spacer 1002 may include an interior lumen through which the trackwire 1014 passes, such that the spacer 1002 is enabled to translate along the trackwire 1014. In some embodiments, the delivery catheter 1006 is decoupled from the spacer 1002 through use of a push rod for pushing the spacer 1002 out of the delivery catheter 1006. Other embodiments may utilize other decoupling means, such as pulling the delivery catheter 1006 proximally back after fixing the position of the spacer 1002, uncoupling a mechanical link, or other means of decoupling from a delivery catheter as known in the art. In some embodiments, the spacer 1002 is delivered within the delivery catheter 1006 or at a distal end of the delivery catheter 1006 in a collapsed form with reduced cross-sectional area relative to an expanded/deployed form. In such embodiments, the spacer 1002 may be filled to an expanded configuration after being positioned in the vicinity of the target area.

In some embodiments, the spacer 1002 is configured to be fillable. For example, the spacer 1002 may include one or more spacer valves for receiving or withdrawing a filler substance, such as a fluid, gel, or foam. In some embodiments, the spacer 1002 is configured to receive a filler substance through a delivery tube, which may be positioned within the delivery catheter 1006 to enable the spacer 1002 to be filled and expanded after it is delivered to the vicinity of the mitral valve annulus 18. For instance, the spacer 1002 may be positioned using the delivery catheter 1006. Then, prior to decoupling and removal of the delivery catheter 1006, a delivery tube within the delivery catheter may be utilized to direct the filling substance into the spacer 1002 (e.g., through one or more spacer valves to which the delivery tube is attachable).

The spacer 1002 may be positioned along the trackwire 1014 so as to reside within the mitral valve annulus 18 through the use of one or more stops disposed on the trackwire 1014. For example, the one or more stops may function to prevent the spacer 1002 from passing distally beyond a particular section of the trackwire 1014. Such stops may be integrally attached to the trackwire 1014, may be mechanically fastened at one or more desired locations during deployment, and/or may be formed through bending or shape-memory action of the trackwire 1014, for example.

In the illustrated embodiment, the integrally attached sensors 1010 and 1012 are able to output pressure measurement data in real-time both during deployment and after deployment of the spacer 1002. For example, each of the sensors 1010 and 1012, as with other sensors described herein, may include a radio frequency ("RF") transmitter for transmitting pressure readings to an external monitoring system. The sensors 1010 and 1012 can thereby continue to monitor atrial and ventricular pressure after the spacer 1002 has been deployed.

Figure 11A:
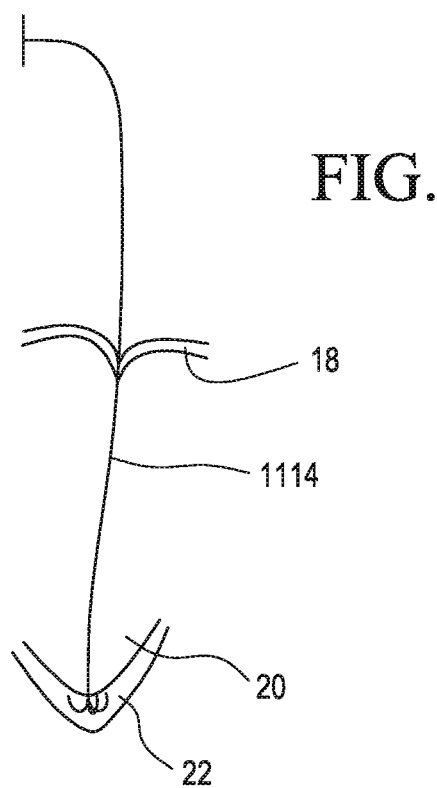
FIGS. 11A-11D illustrate a procedure for deploying an assembly of decoupled sensors and an associated spacer device.
Figure 11B:
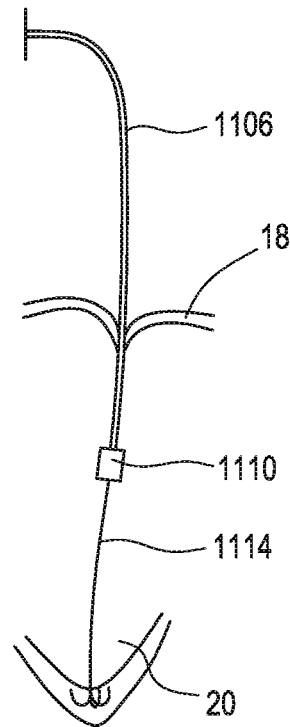

FIGS. 11A-11D illustrate an embodiment of a deployment procedure, from a transfemoral approach, for a spacer and sensor system with sensors 1110 and 1112 decoupled from the spacer 1102. The illustrated embodiment includes components and features similar to those described above with respect to FIGS. 10A and 10B. As shown in FIG. 11A, a trackwire 1114 is directed across the mitral valve annulus 18 into the left ventricle 20 where it is anchored into the myocardium 22 (e.g., at the apex of the left ventricle 20). As shown in FIG. 11B, a ventricular sensor 1110 is subsequently directed through the mitral valve annulus 18 and into the left ventricle 20 via a delivery catheter 1106 as guided by the trackwire 1114. The ventricular sensor 1110 is then crimped onto the trackwire 1114 in the ventricular position, as shown. Alternatively, the ventricular sensor 1110 may be attached through use of an adhesive, through magnetic couplings, and/or through alternative means of mechanically fastening (e.g., crimping).

Figure 11C:
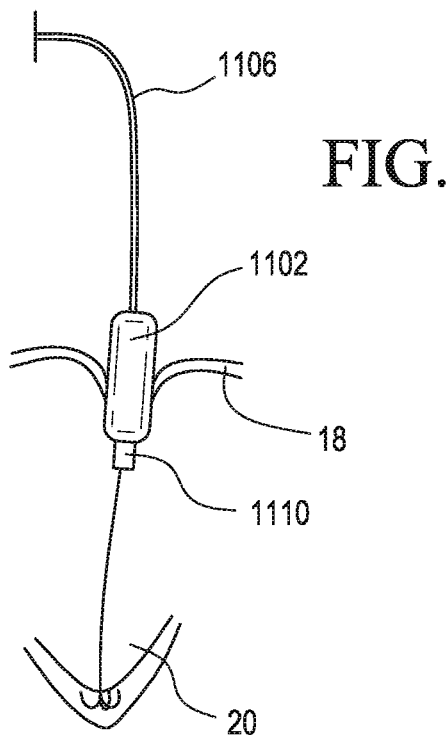

As shown in FIG. 11C, the spacer 1102 is subsequently directed into the mitral valve annulus 18 via delivery catheter 1106. In some embodiments, the spacer 1102 is positioned adjacent to the ventricular sensor 1110. In other embodiments, there is a space between the spacer 1102 and the ventricular sensor 1110. For example, the ventricular sensor 1110 may be positioned further beyond the mitral valve annulus 18 within the left ventricle 20 according to a desired position for ventricular pressure monitoring.

Figure 11D:
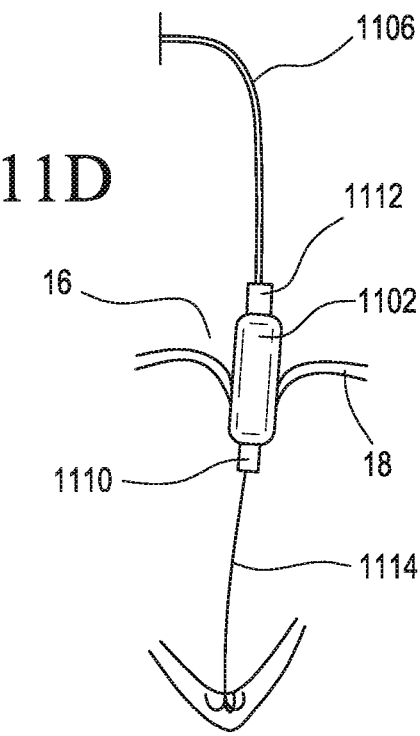

As shown in FIG. 11D, an atrial sensor 1112 is subsequently directed into the left atrium 16 via delivery catheter 1106 according to the path of the trackwire 1114, where it is crimped to the trackwire at a position above the spacer 1102. Alternatively, the ventricular sensor 1110 may be attached through use of an adhesive, through magnetic couplings, and/or through alternative means of mechanically fastening (e.g., crimping). As with the ventricular sensor 1110, the atrial sensor 1112 may be positioned adjacent to the spacer 1102 or may be positioned a distance apart from the spacer 1102, according to a desired pressure monitoring position within the left atrium 16. After deployment, the trackwire 1114 may be cut above at a position above the atrial sensor 1112 and the excess wire (if any) may be coiled up within the left atrium 16.

In some embodiments, one or more sensors are configured as sealed microcapsules including an inductor coil and a pressure sensitive capacitor which form a resonant circuit at a particular frequency. Pressure changes affect the frequency, and frequency changes are tracked and wirelessly transmitted (e.g., as real-time, high-resolution pressure waveforms) to an external receiver enabling intra- and post-procedure monitoring of pressure. In some embodiments, material of sensor capsule is biocompatible (e.g., has anti-inflammatory qualities and body-mimicking properties) and bio-stable by providing antifouling properties and long-term functionality and stability. In some embodiments, the sensor capsules are treated to prevent biofouling and to increase biocompatibility. For example, a metal or polymer surface of a sensor capsule may be coated with a biocompatible coating configured to prevent biofouling, such as small molecules and matrix-targeting enzymes, bactericidal and anti-adhesion coatings (e.g., $TiO_2$ film applied using an atomic layer deposition technique). In some embodiments, the treatment coating includes an immunosuppressant (e.g., Everolimus) to inhibit or minimize tissue growth on the sensor capsule. Other sensors described herein in relation to other embodiments may be similarly configured.

Figure 12A:
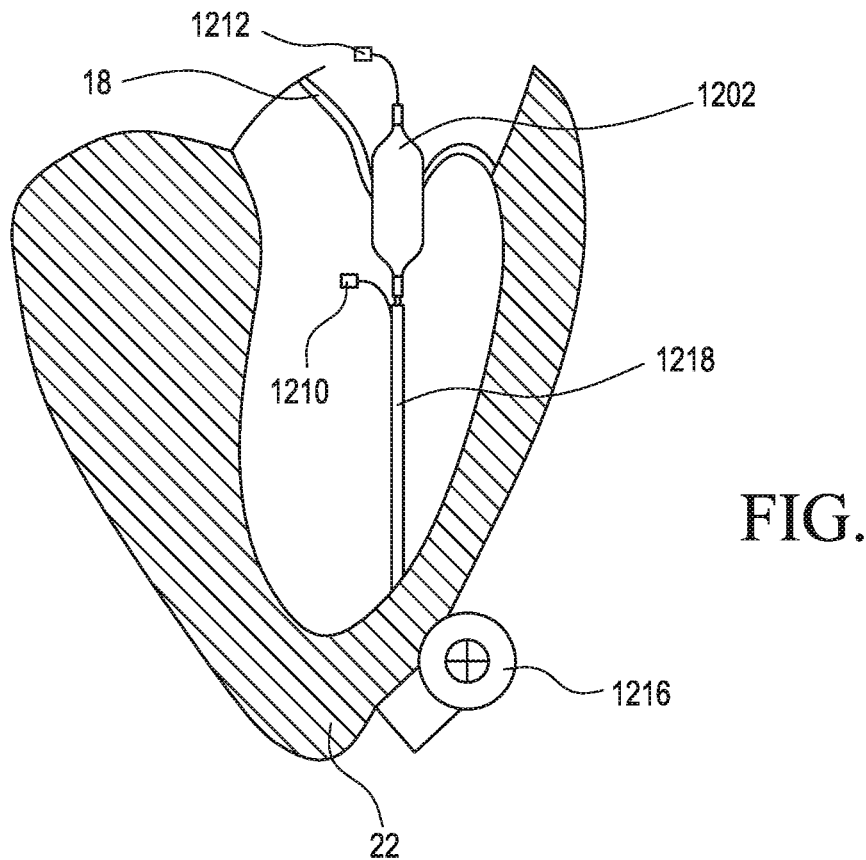
FIGS. 12A and 12B illustrate exemplary embodiments of a spacer device assembly having pressure-monitoring functionality and including an external port for adjusting the spacer device.
Figure 12B:
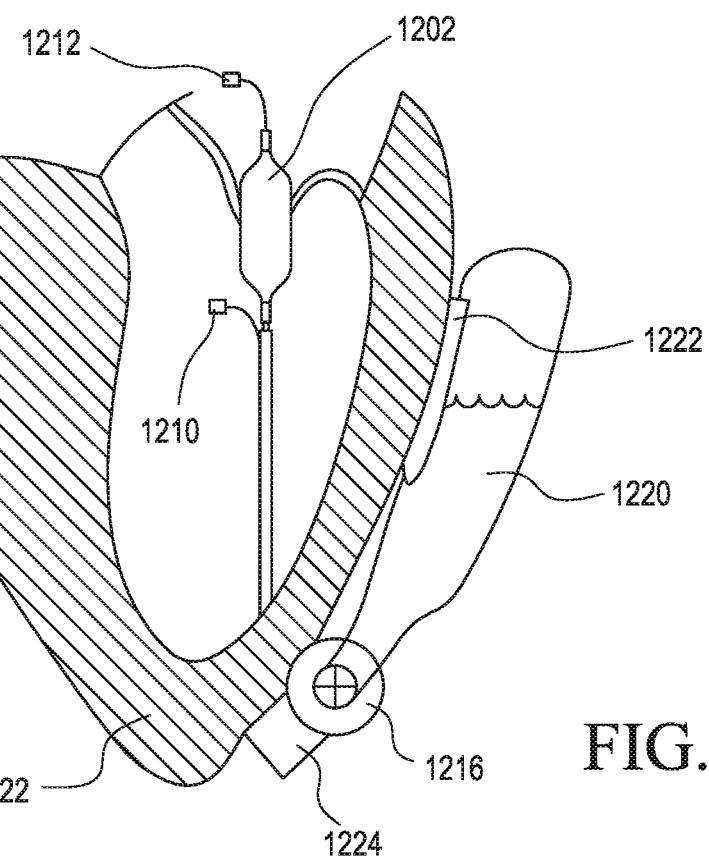

FIGS. 12A and 12B illustrate additional embodiments of spacers configured to provide pressure-sensing functionality. The illustrated spacers may incorporate one or more of the concepts and features of the spacers described above in relation to FIGS. 9-11D. As shown in FIG. 12A, the spacer 1202 includes a ventricular sensor 1210 and an atrial sensor 1212. The spacer 1202 is coupled to a port 1216 positioned external to the myocardium 22 of the heart. The port 1216 provides access to the spacer 1202 such that fluid (e.g., a saline fluid) may be drawn out of the spacer 1202 or added to the spacer 1202 through the conduit 1218. For example, the port 1216 may include one or more pumps and/or valves.

This configuration beneficially enables the spacer 1202 to be fine-tuned during the deployment procedure and even during follow up procedures if necessary. For example, after the spacer 1202 has been positioned, an operator may add or withdraw fluid to give the spacer 1202 a size that sufficiently limits regurgitation while also keeping pressure gradients across the mitral valve annulus 18, as measured by the sensors 1210 and 1212, sufficiently low (e.g., below about 6 mm Hg).

The embodiment illustrated in FIG. 12B includes a self-regulating spacer system configured to automatically adjust the spacer 1202 according to measured pressures as determined by sensors 1210 and 1212. In the illustrated embodiment, the port 1216 is coupled to a fluid reservoir 1220, which may be attached to the exterior of the myocardium 22 with an adhesive patch 1222, as shown, or through other means of attachment, such as mechanical fastening.

The illustrated embodiment also includes a controller 1224 configured to add or withdraw fluid from the spacer 1202 according to pressure readings received from sensors 1210 and 1212. For example, the controller 1224 may include sensor logic circuits that are configured to cause the controller 1224 to actuate the port 1216 to add or withdraw fluid to change the size of the spacer 1202. In some embodiments, the controller 1224 is configured to operate according to one or more predetermined pressure gradient thresholds, such that the controller 1224 is configured to cause the addition or withdrawal of fluid upon receiving pressure measurements from sensor 1210 and/or sensor 1212 that a threshold has been exceeded or that reading have fallen beneath a threshold.

Figure 13A:
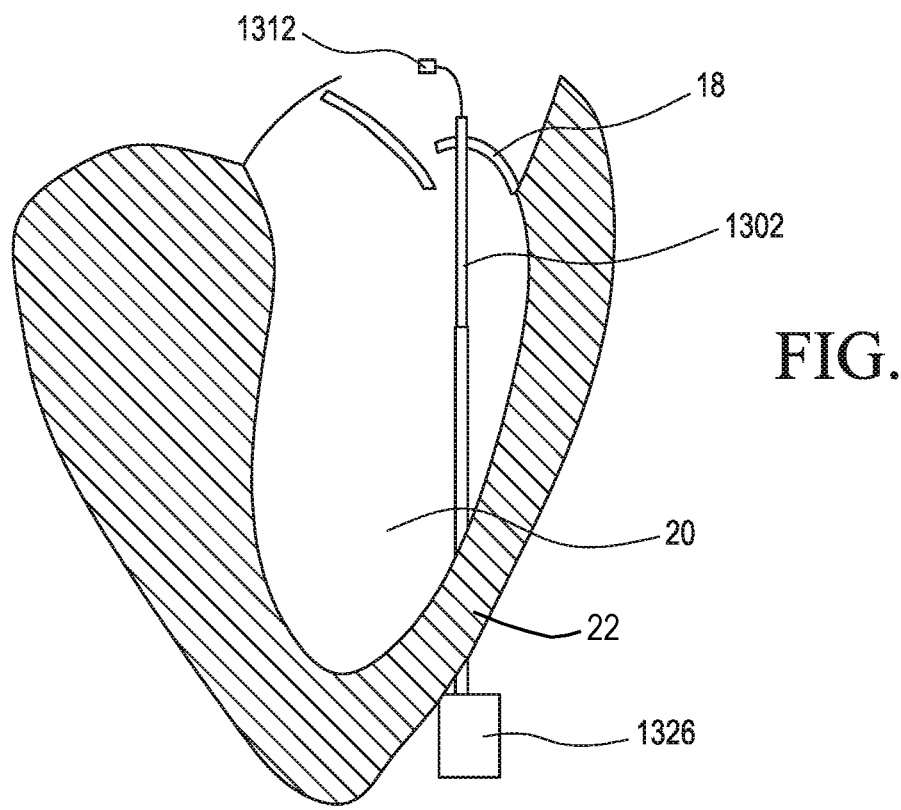
FIGS. 13A and 13B illustrate an exemplary embodiment of a chord replacement device having pressure-monitoring functionality.
Figure 13B:
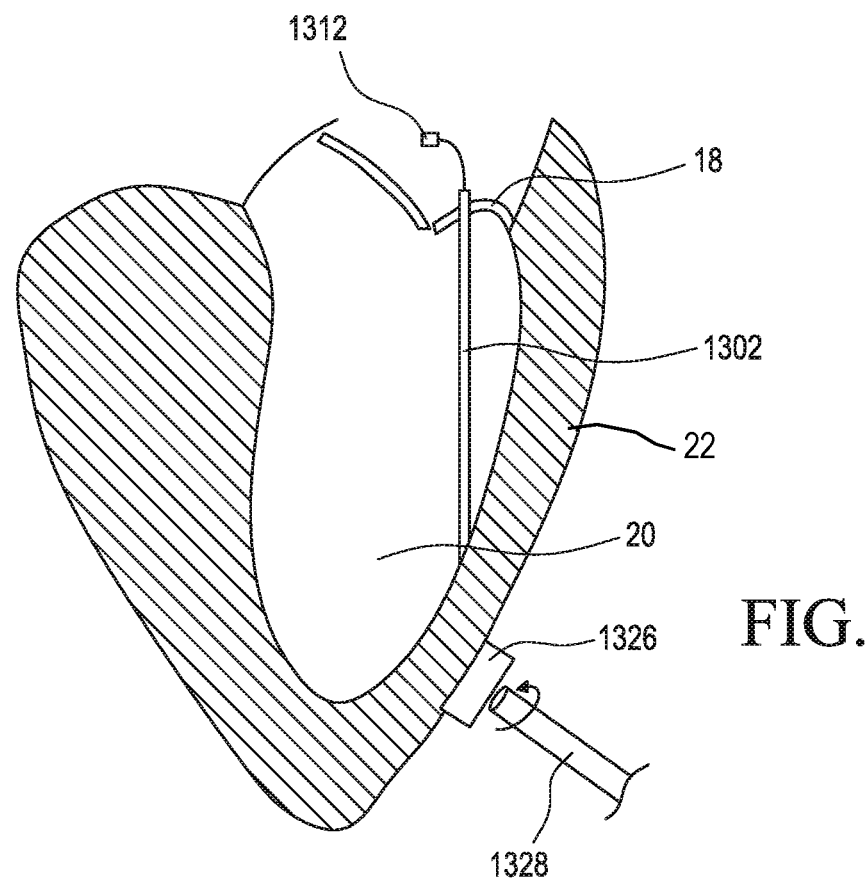

FIGS. 13A and 13B illustrate an embodiment of a chord replacement device 1302 configured to provide intra-procedural and/or post-procedural pressure monitoring. As shown in FIG. 13A, the chord replacement device includes a sensor 1312 positioned so as to be above the mitral valve 18 after the chord replacement device 1302 has been deployed. In this position, the sensor 1312 is capable of measuring the local degree of mitral regurgitation. In some embodiments, a sensor may additionally or alternatively be positioned lower on the replacement chord device 1302, under the mitral valve 18 and within the left ventricle 20.

The chord replacement device 1302 is preferably deployed via a transapical approach using detachable mechanical fixation to a delivery device (e.g., delivery catheter) or using a vacuum fixation device or other delivery method. Pledgets may be deployed and tensioned to an attachment area of the myocardium, preferably at or near the apex of the heart. The chord replacement device 1302 may be formed using one or more of silk, autologous pericardium, polytetrafluoroethylene (e.g., ePTFE, Gore-Tex®), other viseoelastic polymers, or other materials.

In some embodiments, the chord replacement device 1302 is formed from a suitable biocompatible material, such as polytetrafluoroethylene (PTFE). In some embodiments, the chord replacement device 1302 is deployed by attaching a loop or other portion of suture material to an under-supported leaflet and attaching the opposite side of the loop to the myocardium near the ventricular apex, simulating the positioning of a natural chord. In some embodiments, the chord replacement device 1302 may be attached to one or more felt pledgets at the papillary muscles to reinforce the attachment point(s).

The chord replacement device includes an access 1326 extending to the external side of the myocardium 22. The access 1326 is configured to enable adjustment of the length of the chord replacement device 1302, such as through adjustment to a chord tension spool. Thus, if adjustments are required during the deployment procedure or in follow up procedures (e.g., due to material creep and/or enlargement of the heart), an operator may utilize the access 1326 to tighten or loosen the chord replacement device 1302 as necessary. For example, following deployment, pressure measurements transmitted by the sensor 1312 may indicate that the degree of regurgitation is rising, thereby notifying the patient and/or physician that adjustments to the chord replacement device 1302 may be required.

FIG. 13B illustrates the use of a tensioning tool 1328 to adjust the length of the chord replacement device 1302. As shown, the adjustment has increased the tension of the chord replacement device 1302 to bring the leaflets of the mitral valve 18 into a better position for coaptation (relative to the untensioned position shown in FIG. 13A). In some embodiments, the access 1326 also includes a power supply (e.g. battery) and/or transmitter.

Some embodiments may include an additional sensor positioned so as to be disposed within the left ventricle 20 after deployment of the chord replacement device 1302. A single or multiple-sensor system may be associated with a controller to form a self-regulating system similar to the embodiment illustrated in FIG. 12B. For example, the access 1326 may include or be associated with a spool motor operable to adjust the tension of the chord replacement device 1302 according to pressure measurements made by the one or more sensors. In some embodiments, the controller is configured to operate based on predetermined thresholds related to minimizing regurgitation, maintaining safe pressure gradients, and the like.

Figure 14:
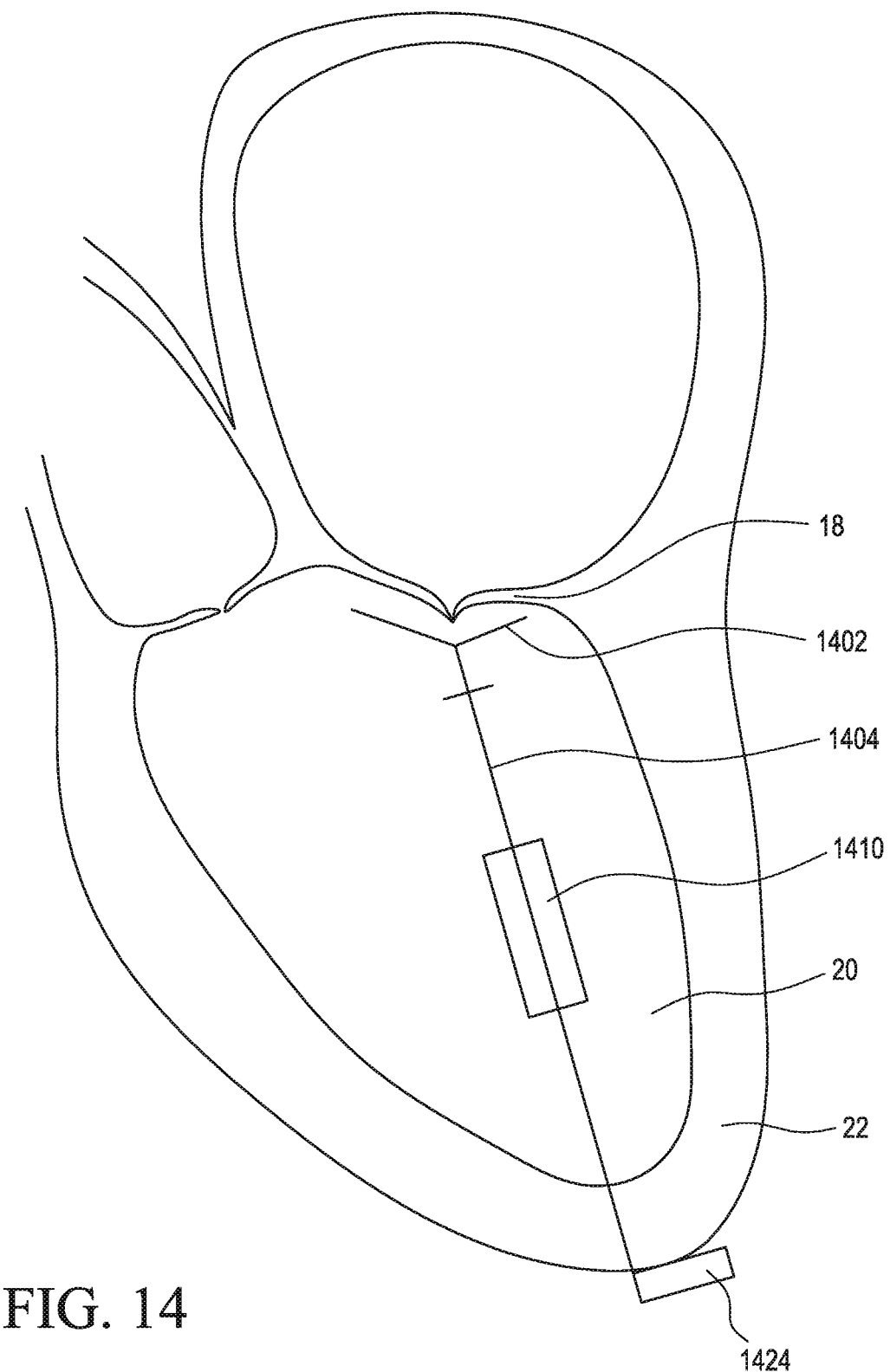
FIG. 14 illustrates an exemplary embodiment of a transapical tether device having pressure-monitoring functionality.

FIG. 14 illustrates an embodiment of an interventional tether 1404 configured to provide pressure-sensing functionality. As shown, the interventional tether 1404 is deployed (e.g., through transapical insertion) within the left ventricle 20, and is coupled to a sensor 1410. The illustrated sensor 1410 is configured as a pressure sensor. In some embodiments, the sensor 1410 may additionally or alternatively be configured to measure tether strain, enabling the conveyance of information related to heart structure remodeling (which may be desirable or undesirable depending on particular circumstances). Pressure and/or strain information may be used to determine adjustments to the tether 1404 and/or to an associated interventional device 1402. As with other sensors described herein, measured data may be transmitted in real-time, and/or may be recorded for later retrieval or transmission. In some embodiments, the interventional tether 1404 is formed from one or more of a metallic material or a polymeric material (e.g., ePTFE). In preferred embodiments, tissue attachment points include one or more pledgets to distribute stresses and forces at the implant/tissue interface.

The interventional device 1402 may be a valve replacement device, annuloplasty ring, valve repair device (e.g., pledgets), or other interventional device described herein which is suitable for use in conjunction with the tether 1404. The illustrated tether 1404 is also associated with a power supply 1424, which is preferably positioned on the external side of the myocardium 22, and which may be used to power the sensor 1410, interventional device 1402, or other elements.

Figure 15A:
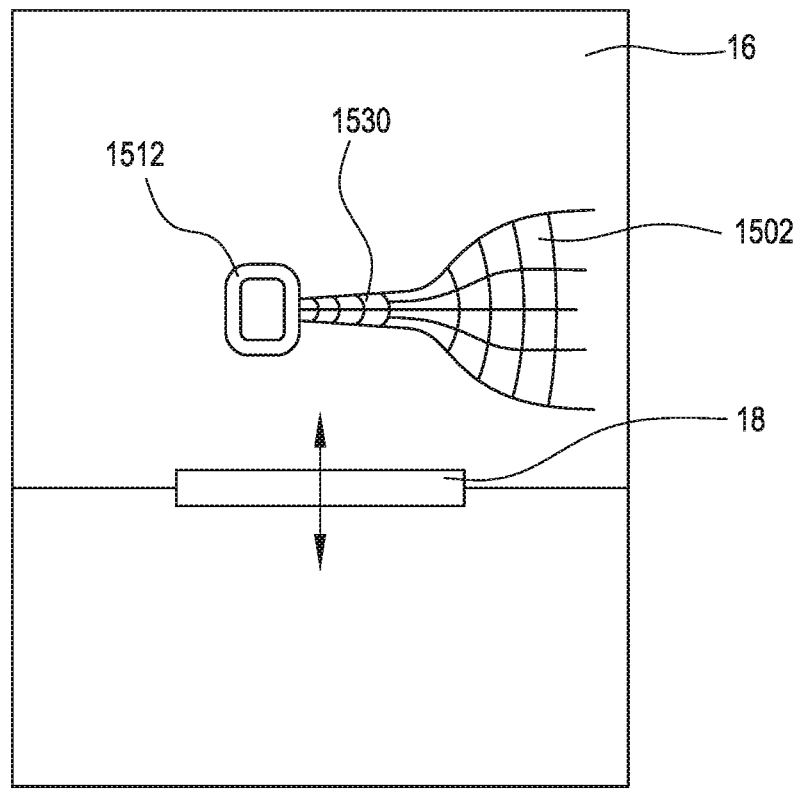
FIGS. 15A and 15B illustrate exemplary embodiments of occluder devices having pressure-monitoring functionality.
Figure 15B:
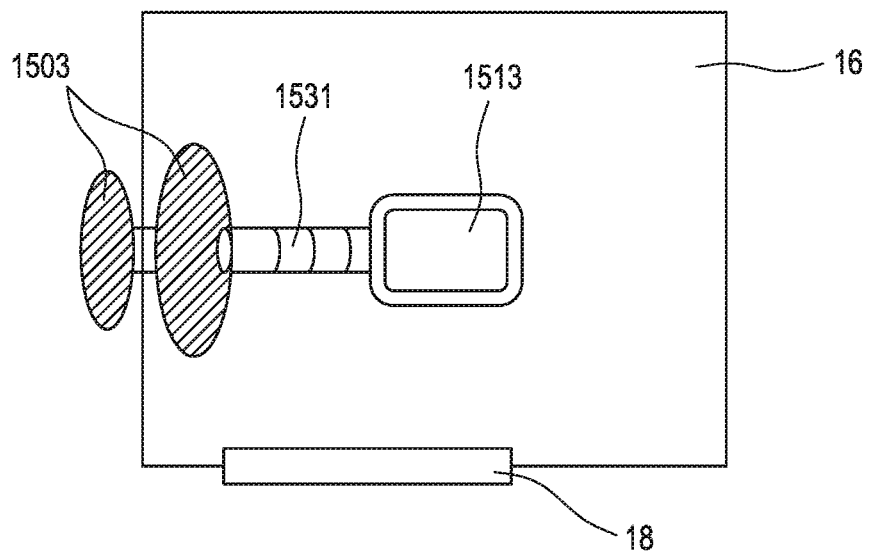

FIGS. 15A and 15B illustrate embodiments of occluder devices configured to provide pressure-sensing functionality. Occluder devices as described herein may be formed from a shape memory material such as nitinol having a polymeric coating or webbing cover (e.g., polyester or other polymer) to function as a tissue growth promotion component. As shown in FIG. 15A, an occluder device 1502 (shown here positioned within the left atrium 16) is configured for use in occluding a left atrial appendage. The occluder device 1502 is coupled to a sensor 1512 via a connector 1530. The connector is configured in size and shape such that when the occluder device 1502 is deployed within a left atrial appendage, the sensor 1512 is extends to a desired position, such as above or in the vicinity of flow across the mitral valve 18.

In some embodiments, the sensor 1512 is integrally attached to the occluder device 1502. In other embodiments, the sensor 1512 is configured to dock onto the occluder device 1502, such as after deployment of the occluder device 1502. In such embodiments, the sensor 1512 may dock onto the occluder device 1502 via one or more of an adhesive patch, magnets, a mechanical linkage, etc. In some embodiments, an occluder device is associated with multiple sensors. For example, multiple sensors may extend from the occluder device to various positions within the left atrium 16.

FIG. 15B illustrates another embodiment of an occluder device 1503 (shown here positioned within the left atrium 16) configured for use in occluding a septal defect. The embodiment shown in FIG. 15B is similar to the embodiment shown in FIG. 15A in several aspects. As shown, the occluder device 1503 is coupled to a sensor 1513 via a connector 1531. The connector 1531 is configured in size and shape so as to position the sensor 1513 in a desired position, such as above or in the vicinity of flow across the mitral valve 18. The sensor 1513 may be integrally attached or docked to the occluder device 1503, as with the sensor 1512 of the embodiment of FIG. 15A. In some embodiments, multiple sensors (e.g., a sensor array) extend from the occluder device 1503 to various desired measurement areas within the heart. The embodiments illustrated in FIGS. 15A and 15B enable the measurement of wall shear stress and/or recirculation of blood flow (sometimes referred to as "smoke" in contrast imaging), which are considered a risk factor for stroke or clotting. For example, flow gradients may be measured using multiple sensor arrays to estimate wall shear stress and recirculation of flow.

Figure 16:
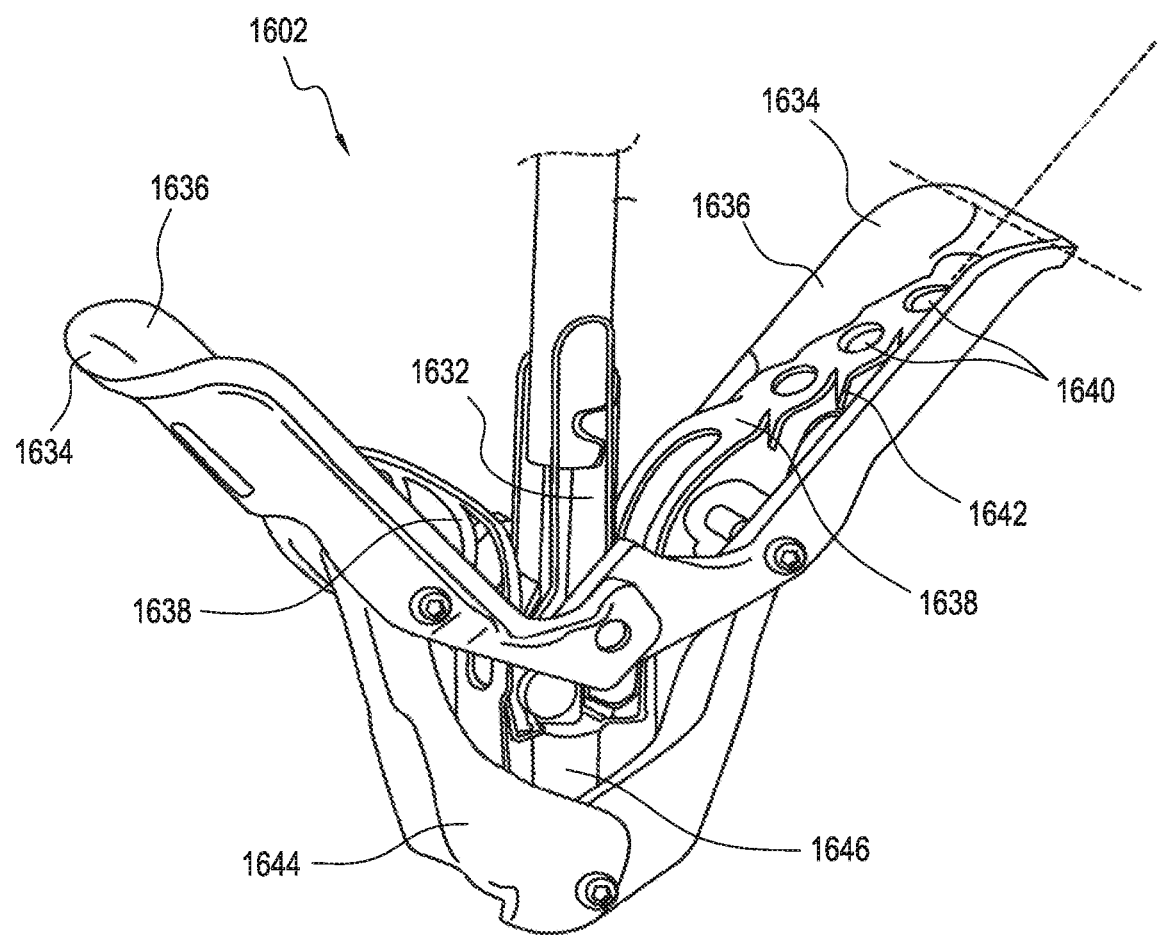
FIG. 16 illustrates an exemplary tissue fixation clip suitable for use with one or more of the pressure-monitoring components described herein.

FIG. 16 illustrates an embodiment of a tissue fixation clip that may be adapted to provide pressure-sensing functionality. The clip 1602 includes a coupling member 1632 and a pair of opposed distal elements 1634, the distal elements 1634 being formed as elongate arms rotatably connected to the coupling member 1632. The engagement surfaces 1636 of the distal elements 1634 have a cupped or concave shape to surface area in contact with tissue and to assist in grasping and holding valve leaflets when deployed.

In an embodiment suitable for mitral valve repair, the transverse width across engagement surfaces 1636 (which determines the width of tissue engaged) is at least about 2 mm, usually 3-10 mm, and preferably about 4-6 mm. The distal elements 1634 are configured to engage a length of tissue of about 4-10 mm, and preferably about 6-8 mm along the longitudinal axis of the distal elements 1634. The distal elements 1634 may include a plurality of openings to enhance grip and to promote tissue ingrowth following implantation.

When deployed, valve leaflets are grasped between the distal elements 1634 and a set of proximal elements 1638, which are resiliently cantilevered from coupling member 1632. The proximal elements 1638 are resiliently biased toward the distal elements 1634. Each of the proximal elements 1638 is shaped and positioned to be at least partially recessed within the concavity of the corresponding distal element 1634 when no tissue is present. The proximal elements 1638 include a plurality of openings 1640 and scalloped side edges 1642 to increase grip on tissue.

The clip 1602 also includes an actuation mechanism 1644 formed from two linking legs each rotatably joined with one of the distal elements 1634 and rotatably joined at an opposite end to a stud 1646. As the stud 1646 is moved axially, the legs of the actuation mechanism 1644 are rotated, which also rotates the distal elements 1634 between closed, open and inverted positions. Likewise, immobilization of the stud 1646 holds the legs of the actuation mechanism 1644 in place to lock the distal elements 1634 in a desired position.

In the open position, the clip 1602 can engage the tissue to be approximated. During deployment in a mitral valve repair procedure, the distal elements 1634 are oriented to be perpendicular to the line of coaptation, and are then positioned so that the engagement surfaces 1636 contact the ventricular surface of the valve leaflets. The proximal elements 1638 remain on the atrial side of the valve leaflets so that the leaflets may be grasped between the proximal elements 1638 and distal elements 1634. Once the clip 1602 has been properly positioned, the proximal elements 1638 are lowered toward the engagement surfaces 1636 (e.g., by releasing tension on attached control lines) so that the leaflets are held therebetween.

After the leaflets have been captured between the proximal elements 1638 and distal elements 1634 in a desired arrangement, the distal elements 1634 may be rotatably moved toward a closed position, and the clip 1602 may be decoupled from a shaft and/or any other delivery mechanisms. Embodiments of tissue fixation clips are further described in U.S. Pat. No. 7,666,204, which is incorporated herein by this reference in its entirety.

Figure 17A:
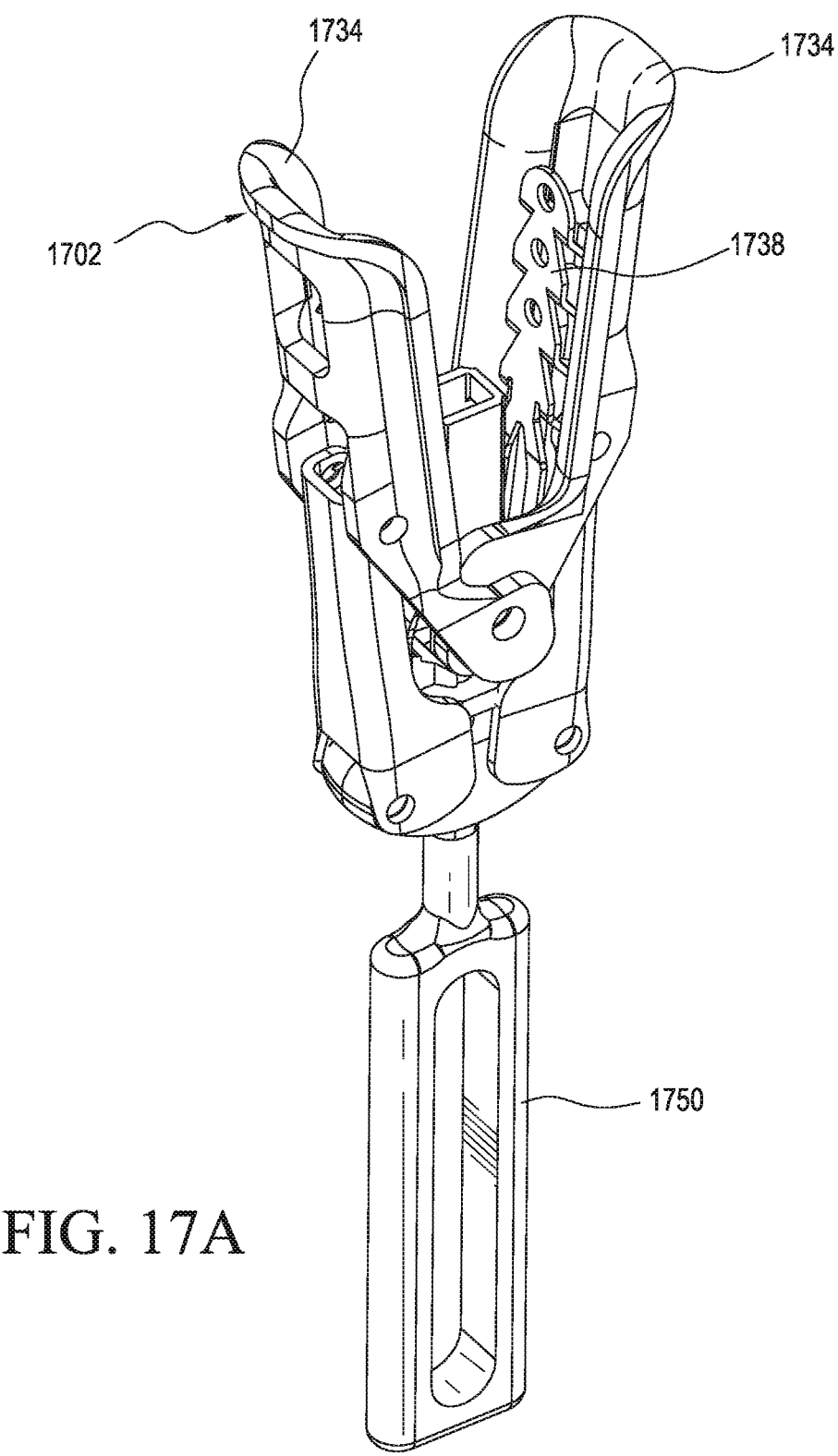
FIGS. 17A-17D illustrate various embodiments of a tissue fixation clip including one or more sensor mounts to provide the clip with pressure-monitoring functionality.

FIGS. 17A-17D illustrate an embodiment of a tissue fixation clip 1702 configured to provide pressure-sensing functionality. As shown in FIG. 17A, the clip 1702 includes a set of distal elements 1734 and a set of proximal elements 1738 biased toward the distal elements 1734 for grasping tissue therebetween. The clip 1702 also includes a ventricular mount 1750 configured for mounting one or more sensors thereon. The ventricular mount 1750 may be integrally attached to the distal section of the clip 1702 with a rigid linkage, or an undulated or coiled flexible connection such that inadvertent tissue contact with the sensor is atraumatic. In other embodiments, the ventricular mount 1750 includes a threaded rod or other attachment means, and is able to be rotated relative to the distal elements 1734 in order to be moved to a position for best measuring flow. When the clip 1702 is deployed and affixed to mitral valve leaflets, the ventricular mount 1750 extends into the left ventricle such that an attached sensor may measure left ventricle pressure.

The ventricular mount 1750 is preferably coupled to the clip 1702 prior to delivery of the clip 1702 to the mitral valve (e.g., with the whole unit delivered through a transfemoral approach). Alternatively, however, the ventricular mount 1750 may be delivered separately (e.g., transapically) and attached to an already delivered clip. For example, a ventricular mount may be delivered transapically to the left ventricle and attached to an already deployed clip by threaded couplings, magnetic couplings, snap-fitting couplings, adhesives or adhesive pads, or other means of attachment.

Figure 17B:
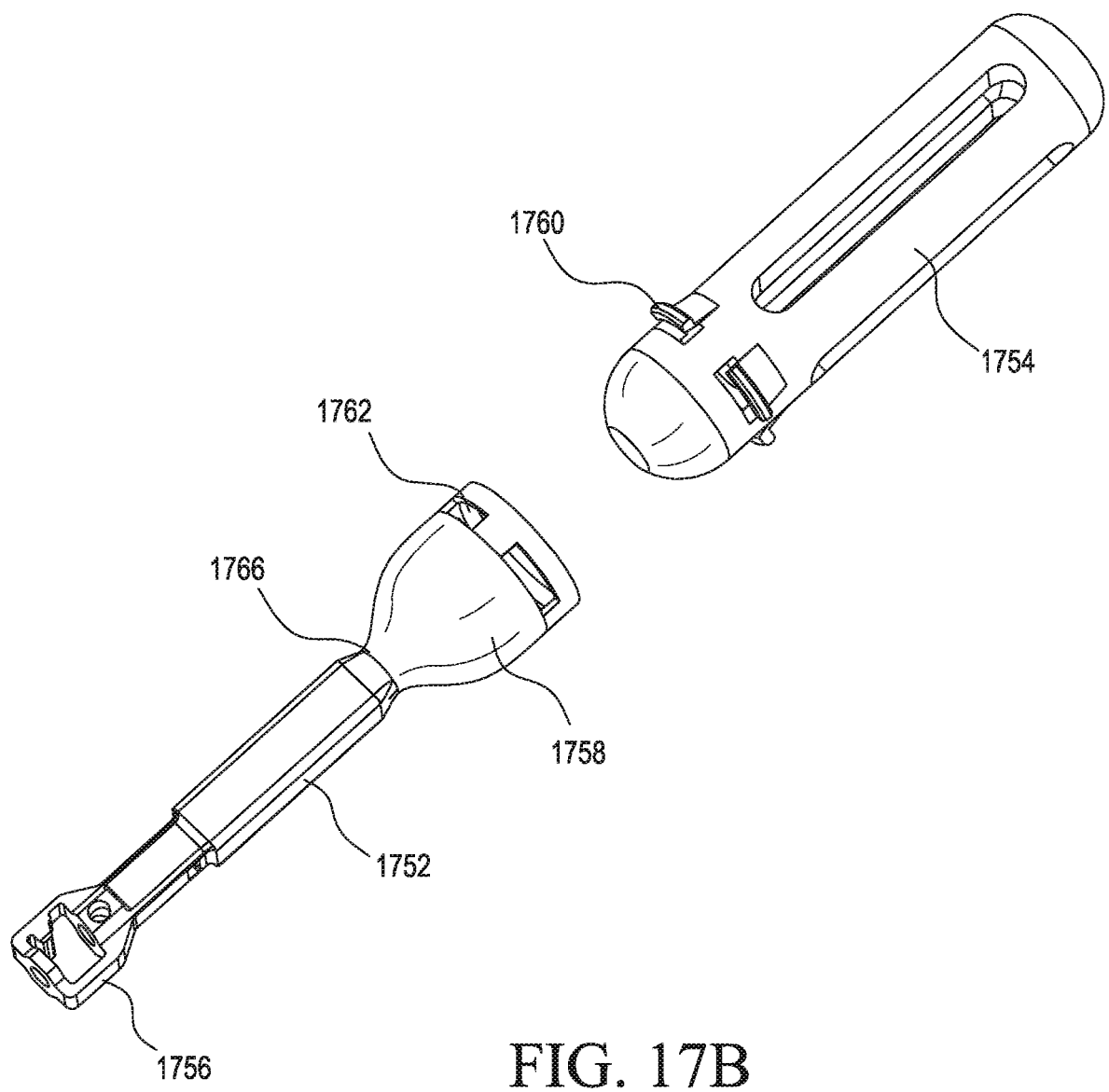
Figure 17C:
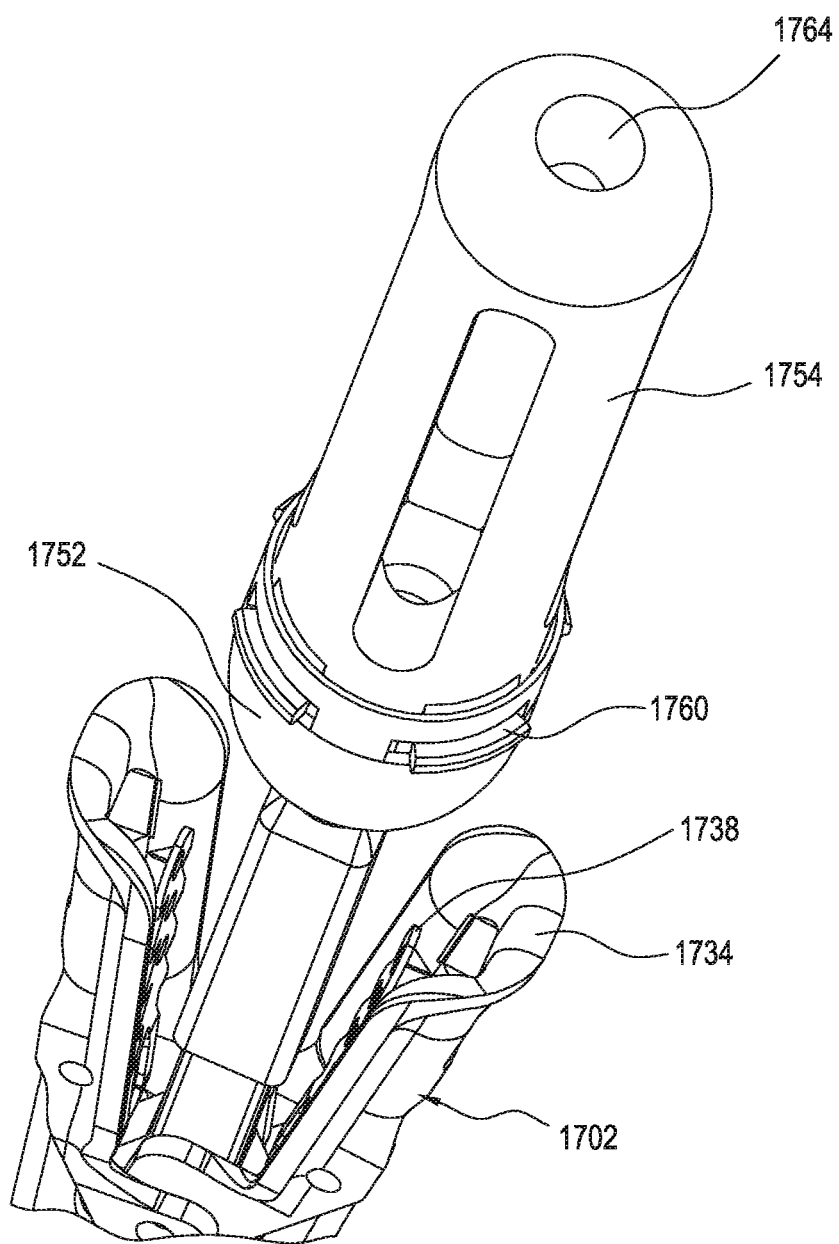

FIGS. 17B and 17C illustrate an embodiment of the clip 1702 configured to include a connector 1752 and an atrial mount 1754. The atrial mount 1754 is configured to receive one or more sensors to enable measurement of atrial pressure during and/or after deployment of the clip 1702. As shown in FIG. 17B, the connector 1752 includes a distal coupler 1756 configured to enable attachment of the connector 1752 to the body of the clip 1702, and a proximal coupler 1758 configured to receive the atrial mount 1754. The illustrated embodiment includes snap arms 1760 and corresponding slots 1762 for coupling the atrial mount 1754 to the connector 1752. Other embodiments may include, additionally or alternatively, one or more threaded couplings, magnetic couplings, clips, adhesives, and/or other fastening means.

In some embodiments, the clip 1702 and the connector 1752 are deployed together as one integral unit. Subsequently, the atrial mount 1754 is delivered to the deployed clip 1702 and is coupled to the connector 1752. In some embodiments, the proximal coupler 1758 is configured to be attachable to a delivery mechanism to enable delivery of the clip 1702 to the mitral valve, and to enable decoupling of the clip 1702 and subsequent attachment of the atrial mount 1754 to the connector 1752.

Typically, the clip 1702 and connector 1752 will be already be deployed when docking of the atrial mount 1754 to the connector 1752 is carried out, meaning that the clip 1702 and connector 1752 will be moving atrially and ventricularly with valve motion during the docking procedure. The connector 1752 and atrial mount 1754 are beneficially configured to enable docking within such a dynamic environment. As shown in FIG. 17C, the atrial mount 1754 includes an orifice 1764 disposed at the proximal end of the mount. The orifice 1764 may be utilized for threading a guidewire through the atrial mount 1754 to aid with alignment during docking. Additionally, or alternatively, the orifice 1764 may be used for attaching the atrial mount 1754 to a delivery catheter for delivery of the atrial mount 1754 to the clip 1702.

The proximal coupler 1758 of the illustrated embodiment includes a flared shape with a neck section 1766 (best seen in FIG. 17B). The size and shape of the connector 1752 allows a snare to be positioned around the connector 1752 to aid in stabilizing the clip 1702 and connector 1752 during docking of the atrial mount 1754 to the connector 1752. For example, during a docking procedure, a snare (e.g., formed from a suture line or other suitable material) may be positioned around the neck section 1766 and may be tensioned proximally in order to proximally pull the connector 1752 and stabilize the clip 1702 and connector 1752 during docking.

Figure 17D:
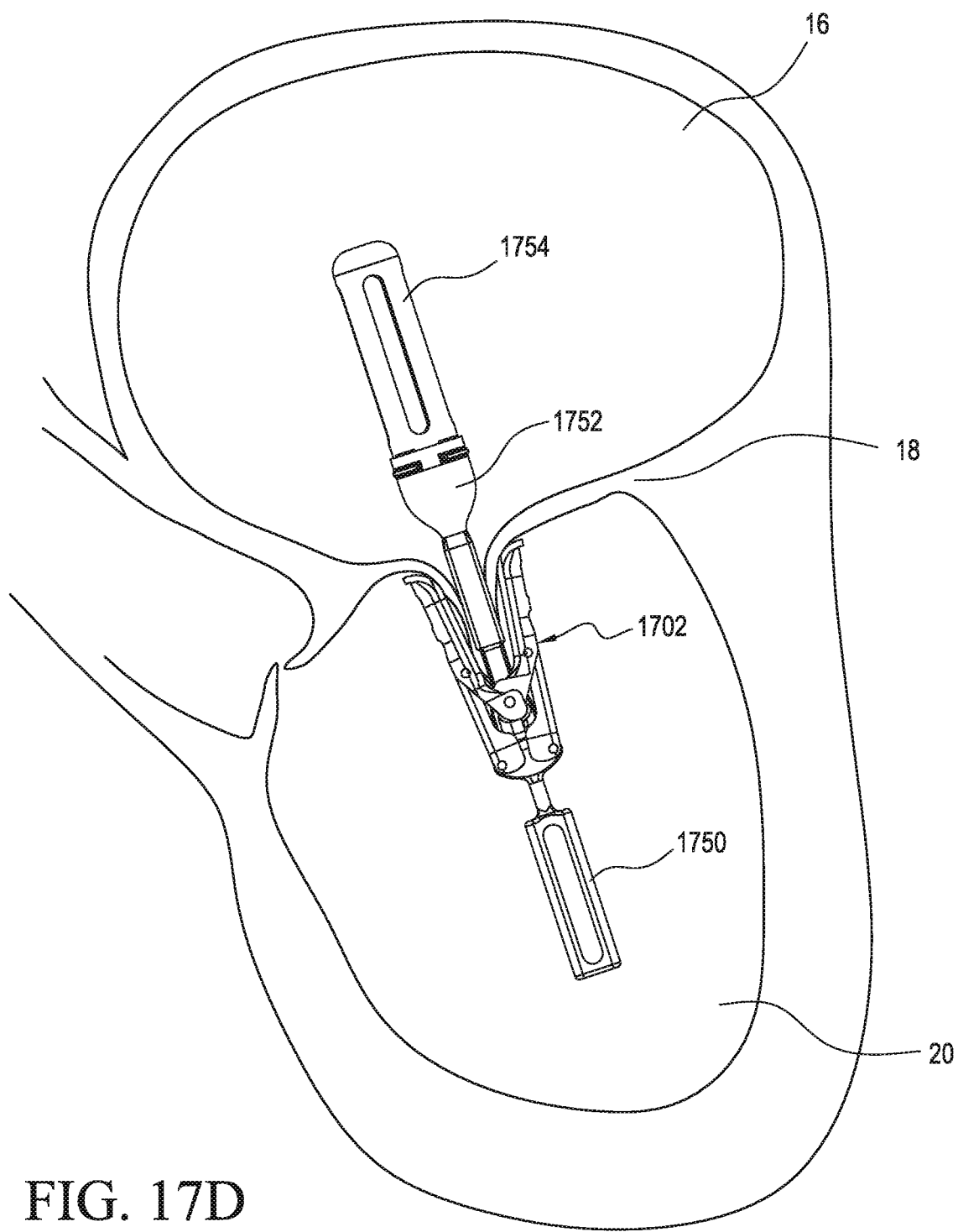

FIG. 17D illustrates an embodiment of the clip 1702 in a deployed state, where the clip 1702 includes both an atrial mount 1754 and a ventricular mount 1750. As shown, as leaflets of the mitral valve 18 are grasped by the clip 1702 the atrial mount 1754 extends into the left atrium 16, and the ventricular mount 1750, extends into the left ventricle 20, the assembly thereby providing pressure measurements on either side of the mitral valve 18. In some embodiments, one or more sections of the clip, particularly the atrial mount 1754 and/or ventricular mount 1750, may be treated to avoid tissue overgrowth and disruption of corresponding sensors. For example, one or more components may include a film of titanium oxide ($TiO_2$ and/or $TiO_3$), other antifouling agent, and/or antiproliferative agent (e.g., Everolimus, Paclitaxel, Sirolimus).

Figure 18:
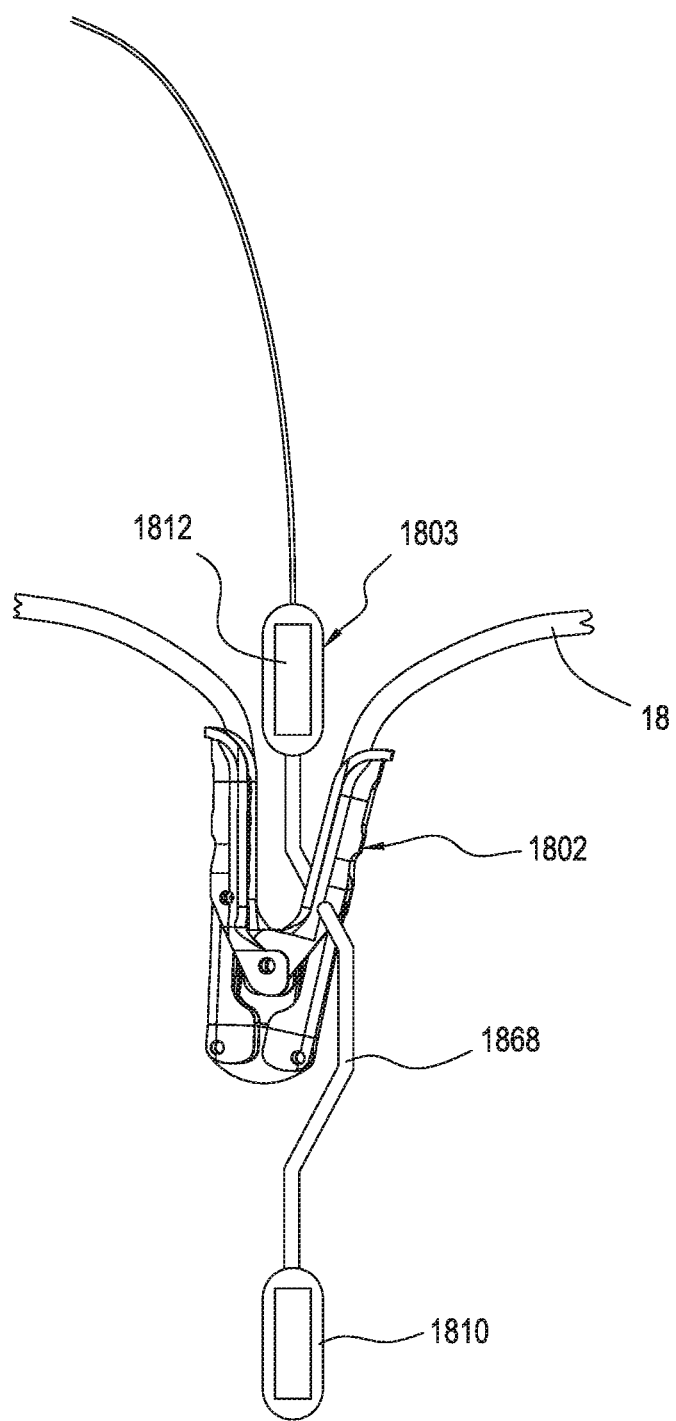
FIG. 18 illustrates an embodiment of a sensor assembly having one or more pressure sensors and configured for docking with a tissue fixation clip.

FIG. 18 illustrates an embodiment of a sensor assembly 1803 configured for deployment with a clip or for attachment to an already deployed clip. In the illustrated embodiment, a sensor assembly 1803 is delivered to an already-deployed clip 1802 (shown grasping the leaflets of the mitral valve 18). As shown, the delivery assembly 1803 includes a ventricular sensor 1810 (or sensor array) and a ventricular sensor 1812 (or sensor array), joined via a connector 1868. The docking of the sensor assembly 1803 to the clip 1802 may include one or more magnetic couplings, snap fittings, threaded connections, adhesives, or other fastening means. The sensor assembly 1803 may be deployed transfemorally or transapically, for example.

Figure 19A:
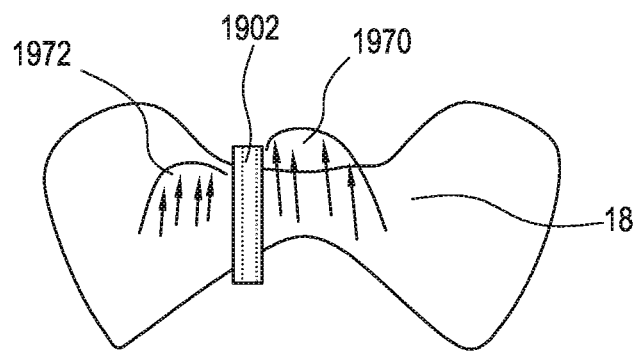
FIGS. 19A-19C illustrate potential procedural adjustments that may be made in order to improve procedural outcomes in light of received pressure measurements using one or more of the embodiments described herein.
Figure 19B:
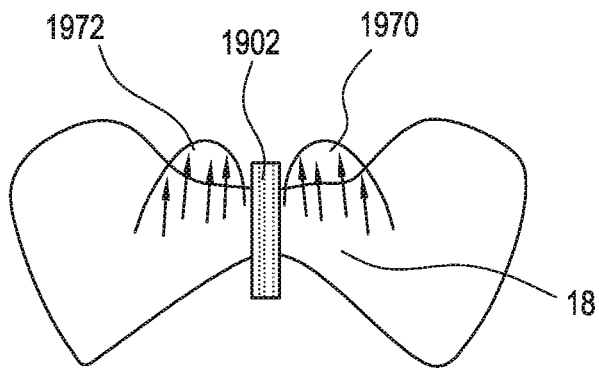
Figure 19C:
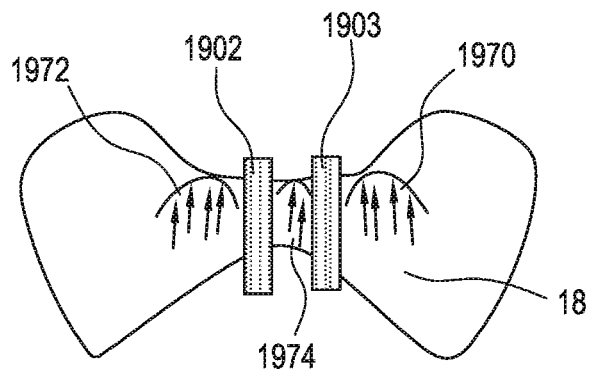

FIGS. 19A-19C illustrate examples of procedural adjustments that may be performed to improve an interventional procedure based on received pressure and/or flow information. FIG. 19A illustrates placement of an interventional device 1902 across a valve 18. As shown, a first flow 1970 on a first side of the device 1902 is greater than a second flow 1972 on a second side of the device 1902, indicating sub-optimal placement of the device. When one or more of the embodiments described herein are utilized to provide pressure-monitoring functionality, and such a flow difference is measured, an operator may make an adjustment to improve the effects of the interventional procedure.

For example, as shown in FIG. 19B, an operator may adjust the position of the interventional device 1902 so that the first flow 1970 and the second flow 1972 are substantially equalized. Alternatively, an operator may deploy one or more additional interventional devices 1903 to equalize the flows 1970 and 1972, as shown in FIG. 19C.

The pressure-monitoring functionality of one or more embodiments described herein may also be utilized for post-procedural pressure monitoring. For example, after deployment of the interventional device 1902 and/or additional interventional device 1903, the first flow 1970, second flow 1972, between flow 1974, and/or other flows may be monitored to determine treatment effectiveness, patient safety, need for subsequent therapy, patient outcomes, and the like.

Figure 20A:
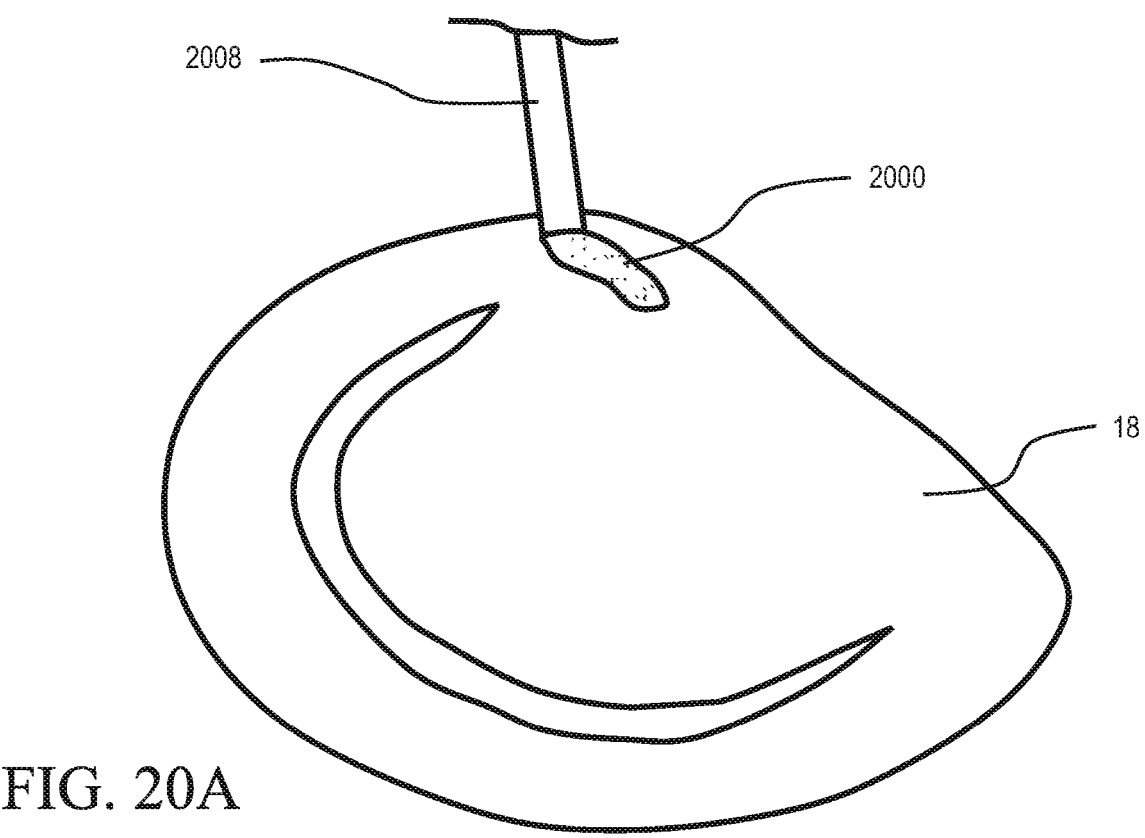
FIGS. 20A-20D illustrate an embodiment of an annuloplasty ring having pressure-monitoring functionality.
Figure 20B:
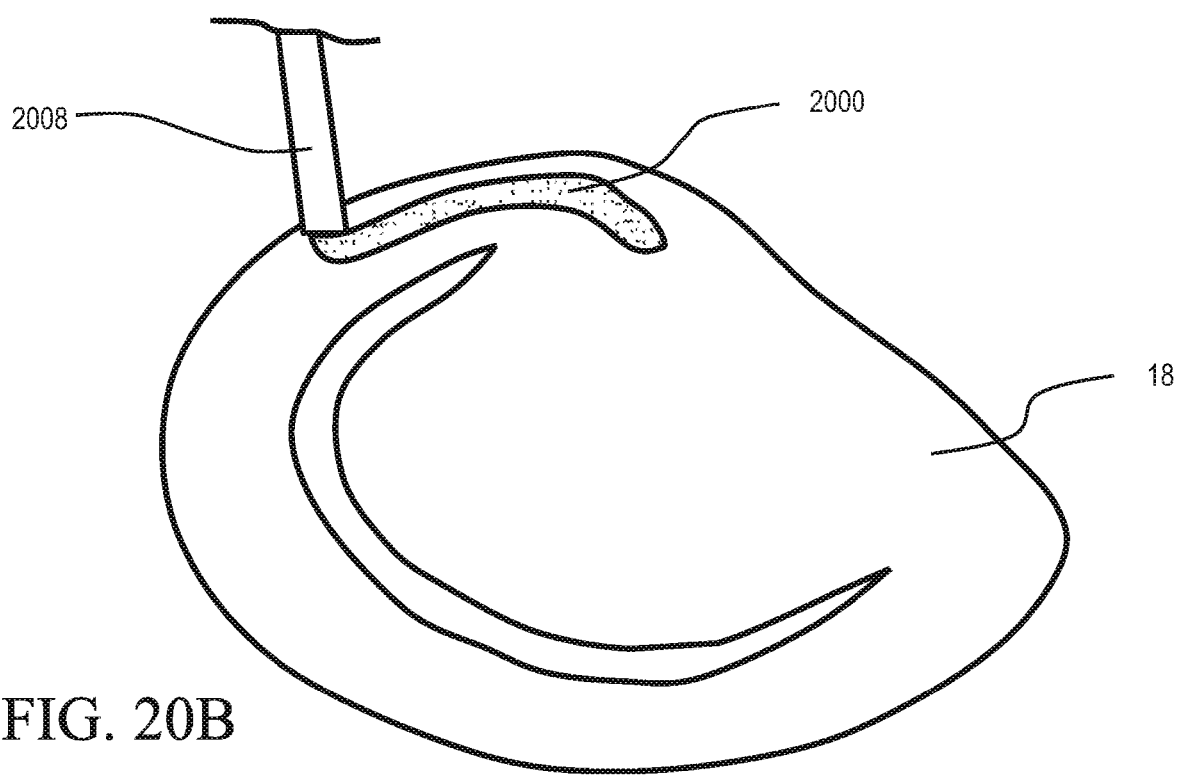
Figure 20C:
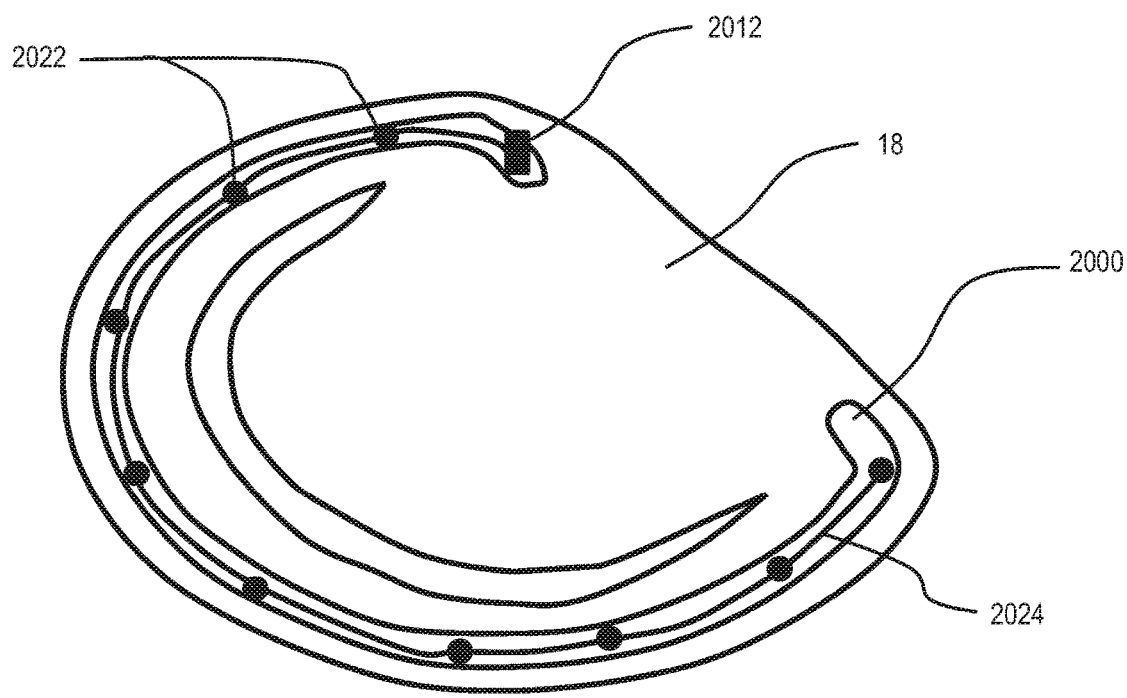

FIGS. 20A-20D illustrate an embodiment of an annuloplasty assembly configured to provide pressure sensing functionality. As shown in FIG. 20A, an annuloplasty device 2000 is configured for delivery to a mitral valve 18 via a delivery catheter 2008. The illustrated embodiment is configured for placement around the perimeter of the valve annulus using a series of sequentially deployed anchors. For example, an initial anchor may be placed, as shown in FIG. 20A, so that the annuloplasty device 2000 may be sequentially positioned along the perimeter of the valve annulus, as shown by FIG. 20B, until the annuloplasty device is fully deployed along the perimeter of the valve annulus, as shown by FIG. 20C.

FIG. 20C illustrates the annuloplasty device 2000 in an anchored position. In FIG. 20C, the annuloplasty device 2000 is shown as transparent in order to better depict the series of anchors 2022 within the annuloplasty device 2000. In the illustrated embodiment, the anchors are connected by a connecting wire 2024, which is threaded through the anchors 2022. The connecting wire 2024 may be tensioned to bring the anchors 2022 closer together to reduce the circumference of the annulus. One or more pressure sensors may also be threaded onto the connecting wire 2024 in order to provide the annuloplasty device 2000 with pressure sensing functionality. In the illustrated embodiment, pressure sensor 2012 is positioned first in the chain of anchors 2022. Additionally, or alternatively, one or more pressure sensors may be positioned along other sections of the annuloplasty device 2000, such as along other sections of the connecting wire 2024. The pressure sensor 2012 may be configured to protrude above the annulus (i.e., to the atrial side) or below (i.e., to the ventricular side) or both.

Figure 20D:
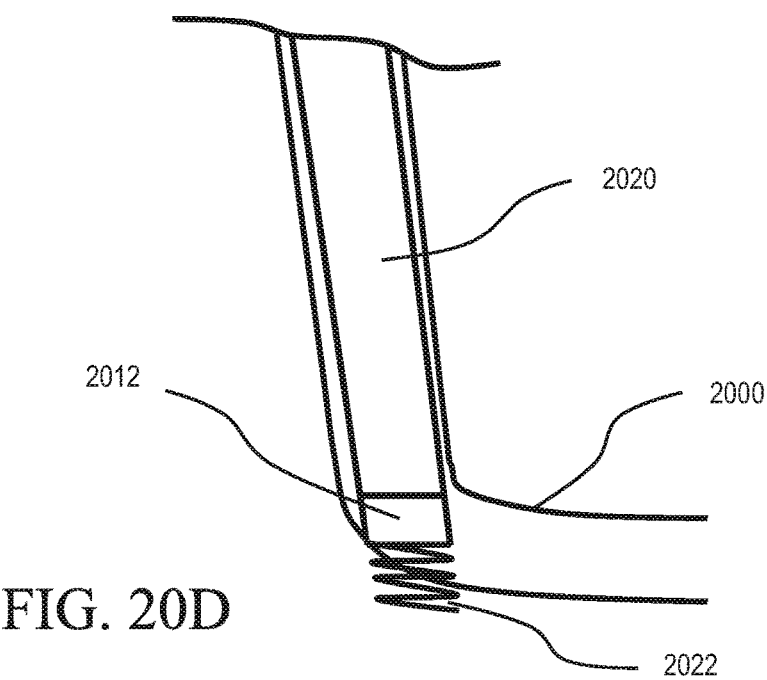

FIG. 20D illustrates a cross-sectional view of the annuloplasty device 2000 showing an anchor catheter 2020 positioned within a lumen of the annuloplasty device 2000. As shown, the anchor catheter 2020 is configured to deliver an anchor 2022 which may be passed through the annuloplasty device 2000 and into adjacent annular tissue to assist in fixing the annuloplasty device 2000. In the illustrated embodiment, the anchor 2022 is configured as a helical screw. Alternatively, an anchor may be configured as a barbed projection, a fishhook shaped member, or other anchoring structure.

In the illustrated embodiment, the pressure sensor 2012 is integrally attached to the anchor 2022, so that the pressure sensor 2012 may be positioned by fixing the anchor 2022 to the annular tissue at the desired location. In other embodiments, one or more pressure sensors may be unanchored. For example, one or more pressure sensors may be threaded along the connecting wire but not configured to be directly anchored into the annular tissue.

In some embodiments, one or more of the foregoing clips, occluders, spacers, or other interventional devices may be treated to provide an antithrombotic effect. For example, an interventional device may be formed from an antithrombotic material and/or coated with an antithrombotic material or compound so as to keep the formation of thrombi within acceptable levels. Additionally, or alternatively, one or more interventional devices described herein may be formed from or coated with an immunosuppressant material configured to prevent tissue growth or other biofouling.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be combinable with elements described in relation to any other embodiment depicted and/or described herein. For example, any element described in relation to a delivery device embodiment, such as those illustrated in FIGS. 3A-8B, may be combinable with any element described in relation to an interventional device embodiment, such as those illustrated in FIGS. 9-18, unless clearly described otherwise.

The present invention may be embodied in other forms, without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A delivery device configured for delivering an interventional device to a targeted treatment area within a body, the delivery device comprising:
   an outer guide catheter having a proximal end and a distal end portion;
   an inner sleeve positioned radially within the outer guide catheter and configured to be translatable within the outer guide catheter, the inner sleeve having a proximal end and a distal end portion;
   a delivery catheter positioned radially within the inner sleeve and configured to be translatable within the inner sleeve, the delivery catheter having a proximal end and a distal end portion;
   an interventional device releasably coupled to the distal end portion of the delivery catheter and configured for delivery through the inner sleeve and outer guide catheter to a targeted treatment area within a body; and at least one sensor coupled to one or more of the distal end portion of the outer guide catheter, the distal end portion of the inner sleeve, or the distal end portion of the delivery catheter, the at least one sensor being configured to enable monitoring of one or more hemodynamic properties of the targeted treatment area during deployment of the interventional device for replacement of a heart valve of a heart or repair of the heart valve using the delivery device;

wherein the at least one sensor includes one or more sensor wires routed in a routing channel formed in a wall of the outer guide catheter, the inner sleeve, or the delivery catheter, and extending from the proximal end and the distal end portion of the outer guide catheter, the inner sleeve, or the delivery catheter; and wherein the interventional device is one of a tissue clip or a replacement valve for treatment of the heart.

2. The delivery device of claim 1, wherein the at least one sensor is configured to measure blood pressure.

3. The delivery device of claim 1, wherein the at least one sensor is configured to measure blood flow.

4. The delivery device of claim 1, wherein the routing channel comprises one or more wall lumens, each wall lumen disposed along a wall of the outer guide catheter, inner sleeve, or delivery catheter.

5. The delivery device of claim 4, wherein the one or more sensor wires are routed along the delivery catheter so as to be distally extendable beyond the delivery catheter.

6. The delivery device of claim 4, wherein the one or more sensor wires are routed along the inner sleeve so as to be distally extendable beyond the inner sleeve.

7. The delivery device of claim 4, wherein the one or more sensor wires are routed along the outer guide catheter so as to be distally extendable beyond the outer guide catheter.

8. The delivery device of claim 1, wherein the at least one sensor includes two or more attached sensors each attached to a point on the outer guide catheter, inner sleeve, or delivery catheter.

9. The delivery device of claim 8, wherein the two or more attached sensors are each attached to the distal end portion of the outer guide catheter, the distal end portion of the inner sleeve, or the distal end portion of the delivery catheter.

10. The delivery device of claim 8, wherein the two or more attached sensors are attached to the outer guide catheter.

11. The delivery device of claim 8, wherein the two or more attached sensors are attached to the inner sleeve.

12. The delivery device of claim 8, wherein the two or more attached sensors are attached to the delivery catheter.

13. The delivery device of claim 8, wherein the two or more attached sensors include a plurality of sensors each attached so as to be at a different longitudinal position when the delivery device is extended into a deploying configuration.

14. The delivery device of claim 1, wherein the at least one sensor includes a plurality of sensors, the plurality of sensors being arranged such that each sensor is positioned at a different section of the targeted treatment area when the delivery device is in a deploying configuration.

15. The delivery device of claim 1, wherein one or more of the outer guide catheter or the inner sleeve include a steering mechanism, the steering mechanism including one or more pullwires each routed through a wall lumen of the outer guide catheter or inner sleeve.

16. The delivery device of claim 15, wherein the targeted treatment area is proximate a mitral valve of the heart, and wherein the delivery system is configured to enable delivery of an interventional tool to the mitral valve through a transfemoral approach.

17. A delivery device for delivering an interventional device to a targeted treatment area within a body, the delivery device comprising:

a steerable outer guide catheter having a proximal end and a distal end portion;

a steerable inner sleeve positioned radially within the outer guide catheter and configured to be translatable within the outer guide catheter, the steerable inner sleeve having a proximal end and a distal end portion;

a delivery catheter positioned radially within the inner sleeve and configured to be translatable within the inner sleeve, the delivery catheter having a proximal end and a distal end portion and being configured to enable delivery of an interventional device through the inner sleeve and outer guide catheter to a targeted treatment area within a body, wherein the targeted treatment area is a heart chamber of a heart; and at least one pressure sensor coupled to one or more of the distal end portion of the steerable outer guide catheter, the distal end portion of the steerable inner sleeve, or the distal end portion of the delivery catheter, the at least one pressure sensor being configured to enable monitoring of blood pressure at the targeted treatment area during deployment of the interventional device for replacement of a heart valve of the heart or repair of the heart valve using the delivery device;

wherein the at least one sensor includes one or more sensor wires routed in a routing channel formed in a wall of the outer guide catheter, the inner sleeve, or the delivery catheter and extending from the proximal end and the distal end portion of the outer guide catheter, the inner sleeve, or the delivery catheter.

18. The delivery device of claim 17, wherein the steerable outer guide catheter and the steerable sleeve each include a steering mechanism including one or more pullwires routed through respective wall lumens of the steerable outer catheter and steerable sleeve.

* * * * *